(12) United States Patent
Masson et al.

(10) Patent No.: US 11,959,860 B2
(45) Date of Patent: Apr. 16, 2024

(54) METHOD FOR THE CLASSIFICATION OF MAPLE SYRUP

(71) Applicant: PRODUCTEURS ET PRODUCTRICES ACÉRICOLES DU QUÉBEC, Longueuil (CA)

(72) Inventors: Jean-Francois Masson, Montreal (CA); Julie Barbeau, Boucherville (CA)

(73) Assignee: PRODUCTEURS ET PRODUCTRICES ACÉRICOLES DU QUÉBEC, Longueuil (CA)

( * ) Notice: Subject to any disclaimer, the term of this patent is extended or adjusted under 35 U.S.C. 154(b) by 733 days.

(21) Appl. No.: 17/052,926

(22) PCT Filed: May 2, 2019

(86) PCT No.: PCT/CA2019/050578
§ 371 (c)(1),
(2) Date: Nov. 4, 2020

(87) PCT Pub. No.: WO2019/210419
PCT Pub. Date: Nov. 7, 2019

(65) Prior Publication Data
US 2022/0034818 A1    Feb. 3, 2022

Related U.S. Application Data

(60) Provisional application No. 62/666,793, filed on May 4, 2018.

(51) Int. Cl.
*G01N 21/78*    (2006.01)
*G01N 21/77*    (2006.01)
*G01N 33/02*    (2006.01)

(52) U.S. Cl.
CPC ............. *G01N 21/78* (2013.01); *G01N 21/77* (2013.01); *G01N 33/02* (2013.01)

(58) Field of Classification Search
CPC ........ G01N 21/77; G01N 21/78; G01N 21/80; G01N 33/02; G01N 2021/7776; G01N 2021/7783; C13B 99/00; C13B 20/00
USPC ............. 436/20, 73, 80, 84, 164; 422/82.05, 422/82.09
See application file for complete search history.

(56) References Cited

U.S. PATENT DOCUMENTS 3,205,076 A  *  9/1965  Wasserman ............... A23L 5/00
                                                        426/48
4,006,032 A  *  2/1977  Hills ....................... A23L 29/30
                                                        426/271

OTHER PUBLICATIONS

Garcia et al. Plos One, vol. 15, No. 8, pp. 1-19, Aug. 20, 2020.*
Camara et al. Journal of Food Science, vol. 84, issue 6, pp. 1538-1546, 2019.*
Forest et al. Analytical Methods, vol. 12, pp. 2460-2468, 2020.*
Bülbül, G. et al. "Portable Nanoparticle-Based Sensors for Food Safety Assessment", Sensors, vol. 15, No. 12, Dec. 5, 2015, pp. 30736-30758.
International Search Report of PCT/CA2019/050578; dated Jul. 17, 2019; Abou-Antoun, Patrick.

* cited by examiner

*Primary Examiner* — Maureen Wallenhorst
(74) *Attorney, Agent, or Firm* — BENOIT & COTE INC.; Mathieu Miron

(57) ABSTRACT

The present document describes a method for the detection of off-flavor maple syrup made from buddy maple sap or maple sap contaminated with buddy maple sap, or off-flavor maple sap. The method involves the measurement of a spectrophotometric property of a nanoparticle reactive with a buddy maple sample having a size of from about 1 nm to about 250 nm contacting a maple syrup or maple sap sample. A change in the spectrophotometric property is associated with an off-flavor maple syrup or maple sap sample, and no change in the spectrophotometric property is associated with a good flavor maple syrup or maple sap sample.

21 Claims, 27 Drawing Sheets

METHOD FOR THE CLASSIFICATION OF MAPLE SYRUP

CROSS-REFERENCE TO RELATED APPLICATIONS

This application is a US National Phase application under 35 USC § 371 of PCT/CA2019/050578, filed May 2, 2019, which claims priority from and the benefit of U.S. Provisional Patent Application No. 62/666,793 filed on May 4, 2018, the specifications of which are hereby incorporated by reference in their entireties.

BACKGROUND

(a) Field

The subject matter disclosed generally relates to a method for the detection of off-flavor maple syrup or maple sap. More specifically, the subject matter relates to a method for the detection of off-flavor maple syrup made from buddy maple sap or maple sap contaminated with buddy maple sap, or off-flavor maple sap by measuring a spectrophotometric property of a nanoparticle.

(b) Related Prior Art

Maple syrup production in Canada accounts for about 80% of the world production, with Quebec accounting for about 90% of the Canadian production (or 72% of world production), which has an impact of $800 million on the gross domestic product (GDP). In the province of Quebec 13,700 producers of maple syrup produce some 300,000 barrels of maple syrup annually, all of which must be quality controlled and categorized (i.e. color, taste, sugar content, etc.). The quality of maple syrup has a direct impact on its market value since the price paid to producers is linked to this quality. Currently, quality assessment of syrups is done by tasters for organoleptic properties and a refractometer is used to measure ° Brix (sugar level) and a spectrophotometer is used to measure absorbance (to assess color). When classifying barrels of maple syrup, syrups with good taste are assigned to the retail market, while the syrups with a different taste (e.g. having taste defects, off-flavor, etc.) will be assigned for industrial markets (i.e. food processing market). Syrups for the industrial market generally have a significant decrease in their market value causing substantial economic losses for the producers and for some having excessive buddy flavor they can even be unmarketable and discarded. Indeed, the annual production of maple syrups assigned to the industrial market can represent 3 to 12% of the annual harvest volume. In a certain percentage of the harvest, a taste defect called buddy taste occurs, hence its nickname of "buddy syrup". This type of defect appears mainly towards the end of the harvest, during the greater temperature changes and when buds are growing on the maple tree. When the off-flavor problem is detected, the syrups with this defect can be treated to mask or remove the buddy taste. More importantly, when buddy syrup is not detected early by tasters, because of the low concentration of problematic compounds present therein, faulty syrups will end up in the retail trade where the buddy off-flavor can reappear after a certain time, thus requiring a recall of the product and the negative economic consequences. Syrups for the industrial market also include syrups having "sappy taste" (i.e. sappy tasting syrup), also referred as having a sap defect.

Studies involving sap chemistry and investigations into physiological changes that occur in sugar maple trees between winter dormancy and bud break have identified the presence of sulphur-based compounds. The sulphur compounds develop naturally in sap as the buds begin to grow. It is believed that these sulphur compounds cause buddy off-flavour in maple syrup. Similar to eggs, onions and cabbage vegetables, sulphur compounds are known to cause odours and flavours that are unwelcome in maple syrup. The sulphur compounds are produced through chemical reactions as the trees begin to use nitrogen-based nutrients. Nitrogen, stored sucrose and other nutrients are utilized to initiate bud development, flowering and early shoot growth as ambient temperatures begin to warm the sugar bush. One of the targeted culprit of this aftertaste has been identified as being an organic compound known as DMDS or Dimethyl disulfide having an unpleasant garlic-like odour.

Currently, maple researchers are testing a number of techniques that might remove the sulphur compounds and buddy flavour from finished syrup, while maintaining the purity and integrity of the syrup. It would be also very beneficial for maple researchers to develop a quick and inexpensive test for the syrup producers to use at the sugar shack, to detect buddy sap prior to initiating or during maple syrup production and wasting fuel and labour.

Therefore there is a need for rapid, simple, effective and affordable analytical techniques for the classification of maple syrups, particularly for detecting maple syrups with different taste, and more specifically compounds causing off-flavor and/or taste defects.

There is also a need for rapid, simple, effective and affordable analytical techniques for the early detection, in maple sap, of compounds causing off-flavor and/or taste defects before maple syrup production that could affect the quality of maple syrup.

SUMMARY

According to an embodiment, there is provided a method for the detection of an off-flavor maple syrup made from buddy maple sap; or an off flavor buddy maple sap comprising measuring a spectrophotometric property of a nanoparticle comprising a nanoparticle reactive with a buddy maple sample having a size of from about 1 nm to about 250 nm contacting a maple sample,
wherein
   a change in the spectrophotometric property is associated with an off-flavor maple syrup or maple sap sample, and
   no change in the spectrophotometric property is associated with a good flavor maple syrup or maple sap sample.

The change in the spectrophotometric property may be compared to a good flavor maple syrup or maple sap sample.

The nanoparticle reactive with a buddy maple sample may be selected from the group consisting of a metallic nanoparticle, a metallic coated nanoparticle, a semi-conducting nanoparticle, or combinations thereof.

The metal of the metallic nanoparticle or the metallic coated nanoparticle may be selected from the group consisting of a gold, copper, iridium, platinum, rhodium nanoparticle, or an alloy thereof, and combinations thereof.

The semi-conducting nanoparticle may be selected from the group consisting of a quantum dot, a carbon dot, and combinations thereof.

The metallic nanoparticle may be in the shape of a sphere, a rods, a rice-grain, a cube, a pyramid, a cage, a disk, or combinations thereof, and preferably a sphere.

The nanoparticle reactive with a buddy maple sample may have a size of about 15 nm.

The nanoparticle reactive with a buddy maple sample may further comprise a coating.

The coating may be an acidic compound.

The acidic compound may be a citrate.

The maple sample may be contacted with a reducing agent prior to or during contact with the nanoparticle.

The reducing agent may be selected from the group consisting of dithiobutylamine, 2-mercaptoetahnol, 2-mercaptoethylamine, cysteine, dithiothreitol (DTT), tris (2-carboxyethyl) phosphine (TCEP), or combinations thereof.

The change in the spectrophotometric property may be a change of color, a change in absorbance, transmittance, diffusion, refractive index or a combination of these measurements.

The change of color may be a change from red to blue.

The change in absorbance may be an increase in absorbance at a wavelength of about 400 nm to about 1000 nm.

The change in absorbance may be a differential absorbance between the absorbance at any wavelength superior to the maximum wavelength of absorption of the nanoparticle in a good flavor sample.

The method of claim 14, wherein the change in absorbance may be a differential absorbance between a wavelength where absorbance remains stable in any maple syrup or maple sap sample and a wavelength where absorbance changes in the off-flavor maple syrup or maple sap sample.

The change in absorbance may be a differential absorbance between any one wavelength ≥561 nm to 1000 nm and any one wavelength between about ≤560 nm wavelength and below.

The change in absorbance may be a differential absorbance between any one wavelength between ≥560 nm to about 1000 nm and absorbance at any one wavelength between about 490 nm to about 560 nm.

The change in absorbance may be a differential absorbance between absorbance at 610 nm and absorbance at any one wavelength between about 490 nm to about 560 nm, and/or between absorbance at 630 nm and absorbance at any one wavelength between bout 490 nm to about 560 nm, and/or between absorbance at 640 nm and absorbance at any one wavelength between about 490 nm to about 560 nm.

The change in absorbance may be a change of a wavelength of maximum absorption to a higher wavelength in the off-flavor maple sample, compared to a good tasting maple sample.

In the method of the present invention, a positive differential absorbance may be associated to an off-flavor maple syrup or maple sap.

In the method of the present invention, a negative differential absorbance may be associated to a good flavor maple syrup or sap.

The off flavor buddy maple sap may be a maple sap contaminated with buddy maple sap, buddy maple syrup or combinations thereof.

The maple sample may be a diluted maple syrup sample, a pure maple syrup sample, a diluted maple sap sample, a pure maple sap sample, a diluted maple sap concentrate sample, or a pure maple sap concentrate sample.

The diluted maple syrup, the diluted maple sap sample or the diluted maple sap concentrate sample may be diluted from about 1:1 to 1:1000 in a solvent.

The solvent may be water or an organic solvent, or combinations thereof.

The concentration of the nanoparticle may be from about 0.1 nM to about 100 nM.

The contacting the maple syrup sample may be from about 1 second to about 30 minutes.

The term "off-flavor maple syrup" or "off-flavor maple sap" is intended to mean a maple syrup or sap sample having a taste that is deemed unacceptable and unpalatable due to its organoleptic properties.

The terms "buddy", "buddy syrup", "buddy maple syrup", "buddy sap" or "buddy maple sap" are generally intended to mean syrups and saps produced from a late run of sugar-maple tree sap gathered after the buds have begun to swell and usually producing maple syrup of poor quality (i.e. buddy syrup) having a characteristic "buddy" taste defect and generally classified as a VR5 syrup in Quebec. Buddy syrup can be described as an unpleasant chocolatey aroma and flavor having a lingering bad aftertaste. Buddy flavor in maple syrup is a food quality issue, not a food safety issue. The taste of bud in the syrup can appear during the season when high temperatures wake up the trees. Therefore, it does not only appear at the end of the season. In this type of syrup, there is a higher concentration of abscisic acid (phytohormone) and amino acids including leucine, methionine, threonine from the metabolism of the tree. There is also a significant decrease in the content of arginine, lysine, glycine and serine.

The terms "sappy taste" and "sappy tasting syrup" are intended to refer to syrup having a sap defect, which is characterized as syrup having a slightly acidic, sweet and sour, pungent, acrid odor. The "sappy" taste is characterized by a slightly rough organoleptic texture, with a slightly acidic, sweet caramelized aroma.

The term "nanoparticle reactive with a buddy maple sample" is intended to mean a nanoparticle or combination of nanoparticles that when put in contact with a normal (good tasting) maple sample will not react, will not change color and/or will not cause a change in the spectrophotometric property(ies) of that sample, and when put into contact with a buddy maple sample will react, will change color and/or will cause a change in the spectrophotometric property(ies) of that sample. The nanoparticle reactive with a buddy maple sample may be any one of a metallic nanoparticle, a metallic coated nanoparticle, a semi-conducting nanoparticle, or combinations thereof that are reactive with a buddy maple sample.

The term "spectrophotometric property" is intended to mean a property related to the reflection, refraction, absorption, diffusion or transmission properties of a material as a function of wavelength. The property may be a qualitative property, such as a color that may be visually assessed by a person, or a quantitative measurement of the reflection, refraction, absorption, diffusion or transmission properties of a material as a function of wavelength and deals with visible, ultraviolet, deep ultraviolet, and near-infrared light.

The term "maple sample" is intended to mean a sample from maple syrup, maple sap, maple sap concentrate, diluted syrup, diluted maple sap, and diluted maple sap concentrate.

The term "maple syrup" is intended to mean syrup made from the sap and/or sap concentrate of certain maple, for example red maple, black maple and particularly sugar maple, as known in the art.

The term "maple sap" is intended to mean the fluid transported in xylem cells (vessel elements or tracheids) or phloem sieve tube elements of the maple plant, which is used in the production of maple syrup. Maple sap is also referred to in the art as "maple water", which is distinct from the strict water content of maple sap (or in other words, water from sap), which is removed from maple sap, for example during reverse osmosis of maple sap. As used herein, the term maple sap also encompasses maple sap concentrate (or concentrated maple sap). The term "maple sap concentrate" is intended to mean a concentrated form of maple sap which is obtained by various means used to remove/eliminate a significant portion of water from maple sap, such as boiling, freezing, reverse osmosis, filtration with membranes (e.g. microfiltration and nanofiltration membranes).

The terms "diluted maple syrup" and "diluted maple sap concentrate" are intended to mean maple syrup or maple sap concentrate that is diluted in a solvent, such as water. For example, in embodiments, maple syrup and maple sap concentrate may be used in the preparation of maple flavored beverages, which are encompassed under maple samples.

Features and advantages of the subject matter hereof will become more apparent in light of the following detailed description of selected embodiments, as illustrated in the accompanying figures. As will be realized, the subject matter disclosed and claimed is capable of modifications in various respects, all without departing from the scope of the claims. Accordingly, the drawings and the description are to be regarded as illustrative in nature, and not as restrictive and the full scope of the subject matter is set forth in the claims.

BRIEF DESCRIPTION OF THE DRAWINGS

Further features and advantages of the present disclosure will become apparent from the following detailed description, taken in combination with the appended drawings, in which.

DETAILED DESCRIPTION

Figure 1:
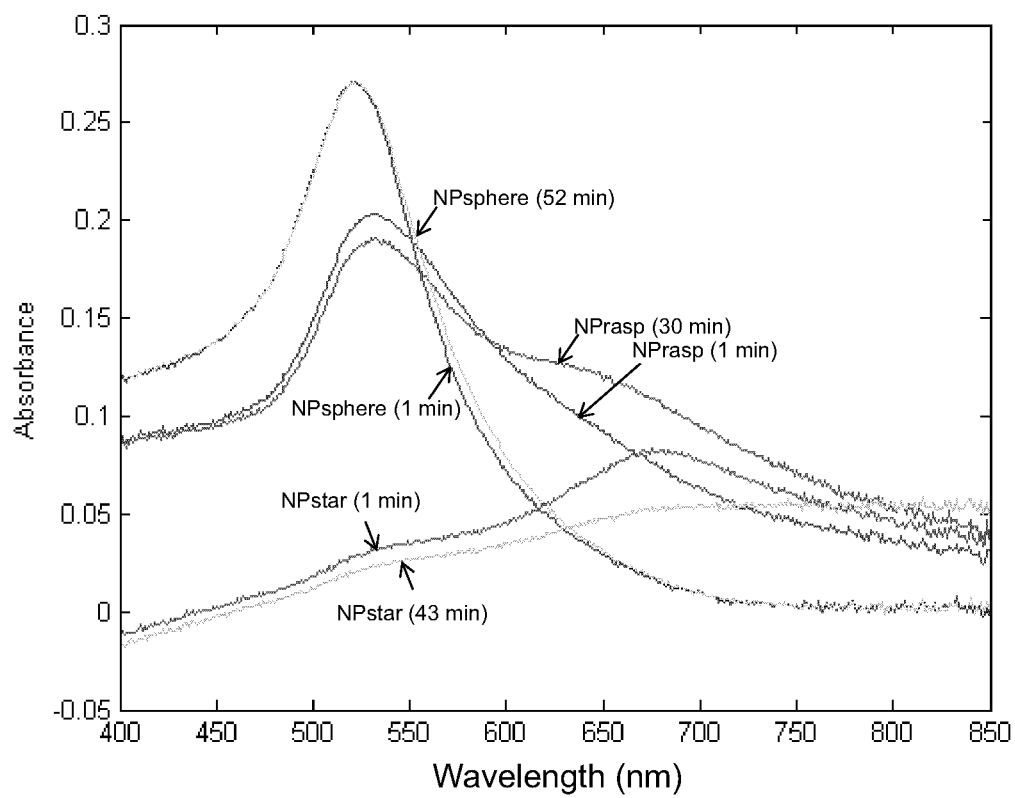
FIG. 1 illustrates the extinction spectra (UV-Vis) of star-(NPstar), raspberry- (NPrasp) and spherical-shaped (NP-sphere) gold nanoparticles in good-tasting maple syrup diluted 10-fold.

According to an embodiment of the present invention, there is disclosed a quick, simple and inexpensive method for detecting buddy tasting syrups, saps and sap concentrates, i.e. syrups, saps or sap concentrates containing an unsavory off-flavor.

In a first embodiment there is disclosed a method for the detection of off-flavor maple syrup made from buddy maple sap; maple sap contaminated with buddy maple sap; or off-flavor maple sap. The method comprises measuring a spectrophotometric property of a nanoparticle contacting a maple sample. The maple sap and off-flavor maple sap may be concentrated versions thereof, as indicated above.

The off flavor buddy maple sap may be from sap contaminated with buddy maple sap, buddy maple syrup or combinations thereof.

Nanoparticles encompasses metallic nanoparticles (gold, copper, iridium, platinum, rhodium, among others; and their alloys) and semi-conducting nanoparticles (quantum dots, carbon dots, among others). The shape of the nanoparticles encompasses spheres, rods, rice, cubes, pyramids, cages, disks, among others. When measuring the spectrophotometric property, a change in this spectrophotometric property is associated with an off-flavor maple sample, and no change in the spectrophotometric property is associated with a good flavor maple sample. In some embodiments, the change in the spectrophotometric property may be compared to a good flavor maple sample.

According to an embodiment, the spherical nanoparticle used in the present invention may have a size of from about 1 nm to about 250 nm, or from about 5 nm to about 250 nm, or from about 10 nm to about 250 nm, or from about 15 nm to about 250 nm, or from about 20 nm to about 250 nm, or from about 25 nm to about 250 nm, or from about 30 nm to about 250 nm, or from about 40 nm to about 250 nm, or from about 50 nm to about 250 nm, or from about 60 nm to about 250 nm, or from about 70 nm to about 250 nm, or from about 80 nm to about 250 nm, or from about 90 nm to about 250 nm, or from about 100 nm to about 250 nm, or from about 125 nm to about 250 nm, or from about 150 nm to about 250 nm, or from about 175 nm to about 250 nm, or from about 200 nm to about 250 nm, or from about 225 nm to about 250 nm, or from 1 nm to about 225 nm, or from about 5 nm to about 225 nm, or from about 10 nm to about 225 nm, or from about 15 nm to about 225 nm, or from about 20 nm to about 225 nm, or from about 25 nm to about 225 nm, or from about 30 nm to about 225 nm, or from about 40 nm to about 225 nm, or from about 50 nm to about 225 nm, or from about 60 nm to about 225 nm, or from about 70 nm to about 225 nm, or from about 80 nm to about 225 nm, or from about 90 nm to about 225 nm, or from about 100 nm to about 225 nm, or from about 125 nm to about 225 nm, or from about 150 nm to about 225 nm, or from about 175 nm to about 225 nm, or from about 200 nm to about 225 nm, or from 1 nm to about 200 nm, or from about 5 nm to about 200 nm, or from about 10 nm to about 200 nm, or from about 15 nm to about 200 nm, or from about 20 nm to about 200 nm, or from about 25 nm to about 200 nm, or from about 30 nm to about 200 nm, or from about 40 nm to about 200 nm, or from about 50 nm to about 200 nm, or from about 60 nm to about 200 nm, or from about 70 nm to about 200 nm, or from about 80 nm to about 200 nm, or from about 90 nm to about 200 nm, or from about 100 nm to about 200 nm, or from about 125 nm to about 200 nm, or from about 150 nm to about 200 nm, or from 1 nm to about 175 nm, or from about 5 nm to about 175 nm, or from about 10 nm to about 175 nm, or from about 15 nm to about 175 nm, or from about 20 nm to about 175 nm, or from about 25 nm to about 175 nm, or from about 30 nm to about 175 nm, or from about 40 nm to about 175 nm, or from about 50 nm to about 175 nm, or from about 60 nm to about 175 nm, or from about 70 nm to about 175 nm, or from about 80 nm to about 175 nm, or from about 90 nm to about 175 nm, or from about 100 nm to about 175 nm, or from about 125 nm to about 175 nm, or from about 150 nm to about 175 nm, or from 1 nm to about 150 nm, or from about 5 nm to about 150 nm, or from about 10 nm to about 150 nm, or from about 15 nm to about 150 nm, or from about 20 nm to about 150 nm, or from about 25 nm to about 150 nm, or from about 30 nm to about 150 nm, or from about 40 nm to about 150 nm, or from about 50 nm to about 150 nm, or from about 60 nm to about 150 nm, or from about 70 nm to about 150 nm, or from about 80 nm to about 150 nm, or from about 90 nm to about 150 nm, or from about 100 nm to about 150 nm, or from about 125 nm to about 150 nm, or from 1 nm to about 125 nm, or from about 5 nm to about 125 nm, or from about 10 nm to about 125 nm, or from about 15 nm to about 125 nm, or from about 20 nm to about 125 nm, or from about 25 nm to about 125 nm, or from about 30 nm to about 125 nm, or from about 40 nm to about 125 nm, or from about 50 nm to about 125 nm, or from about 60 nm to about 125 nm, or from about 70 nm to about 125 nm, or from about 80 nm to about 125 nm, or from about 90 nm to about 125 nm, or from about 100 nm to about 125 nm, or from 1 nm to about 100 nm, or from about 5 nm to about 100 nm, or from about 10 nm to about 100 nm, or from about 15 nm to about 100 nm, or from about 20 nm to about 100 nm, or from about 25 nm to about 100 nm, or from about 30 nm to about 100 nm, or from about 40 nm to about 100 nm, or from about 50 nm to about 100 nm, or from about 60 nm to about 100 nm, or from about 70 nm to about 100 nm, or from about 80 nm to about 100 nm, or from about 90 nm to about 100 nm, or from 1 nm to about 90 nm, or from about 5 nm to about 90 nm, or from about 10 nm to about 90 nm, or from about 15 nm to about 90 nm, or from about 20 nm to about 90 nm, or from about 25 nm to about 90 nm, or from about 30 nm to about 90 nm, or from about 40 nm to about 90 nm, or from about 50 nm to about 90 nm, or from about 60 nm to about 90 nm, or from about 70 nm to about 90 nm, or from about 80 nm to about 90 nm, or from 1 nm to about 80 nm, or from about 5 nm to about 80 nm, or from about 10 nm to about 80 nm, or from about 15 nm to about 80 nm, or from about 20 nm to about 80 nm, or from about 25 nm to about 80 nm, or from about 30 nm to about 80 nm, or from about 40 nm to about 80 nm, or from about 50 nm to about 80 nm, or from about 60 nm to about 80 nm, or from about 70 nm to about 80 nm, or from 1 nm to about 70 nm, or from about 5 nm to about 70 nm, or from about 10 nm to about 70 nm, or from about 15 nm to about 70 nm, or from about 20 nm to about 70 nm, or from about 25 nm to about 70 nm, or from about 30 nm to about 70 nm, or from about 40 nm to about 70 nm, or from about 50 nm to about 70 nm, or from about 60 nm to about 70 nm, or from 1 nm to about 60 nm, or from about 5 nm to about 60 nm, or from about 10 nm to about 60 nm, or from about 15 nm to about 60 nm, or from about 20 nm to about 60 nm, or from about 25 nm to about 60 nm, or from about 30 nm to about 60 nm, or from about 40 nm to about 60 nm, or from 50 nm to about 60 nm, or from 1 nm to about 50 nm, or from about 5 nm to about 50 nm, or from about 10 nm to about 50 nm, or from about 15 nm to about 50 nm, or from about 20 nm to about 50 nm, or from about 25 nm to about 50 nm, or from about 30 nm to about 50 nm, or from about 40 nm to about 50 nm, or from 1 nm to about 40 nm, or from about 5 nm to about 40 nm, or from about 10 nm to about 40 nm, or from about 15 nm to about 40 nm, or from about 20 nm to about 40 nm, or from about 25 nm to about 40 nm, or from about 30 nm to about 40 nm, or from 1 nm to about 30 nm, or from about 5 nm to about 30 nm, or from about 10 nm to about 30 nm, or from about 15 nm to about 30 nm, or from about 20 nm to about 30 nm, or from about 25 nm to about 30 nm, or from 1 nm to about 25 nm, or from about 5 nm to about 25 nm, or from about 10 nm to about 25 nm, or from about 15 nm to about 25 nm, or from about 20 nm to about 25 nm, or from 1 nm to about 20 nm, or from about 5 nm to about 20 nm, or from about 10 nm to about 20 nm, or from about 15 nm to about 20 nm, or from 1 nm to about 15 nm, or from about 5 nm to about 15 nm, or from about 10 nm to about 15 nm, or from 1 nm to about 10 nm, or from about 5 nm to about 10 nm, or from 1 nm to about 5 nm, or 1, 5, 10, 15, 20, 25, 30, 40, 50, 60, 70, 80, 90, 100, 125, 150, 175, 200, 225, 250 nm.

In an embodiment, the size of the spherical nanoparticle may be about 15 nm.

In an embodiment, the nanoparticle reactive with a buddy maple sample may further comprise a coating. For example, the nanoparticle may be coated with an acidic compound, such as a citrate compound, which may be obtained from citric acid, sodium or calcium citrate, for example.

In embodiments of the present invention, the spherical nanoparticle may be a gold nanoparticle (AuNP).

According to another embodiment, to increase the sensitivity of the method of the present invention, a reducing agent may be added to the maple samples to facilitate adsorption of the molecules associated with the taste defect onto the nanoparticles. In embodiments, the maple sample may be contacted with a reducing agent prior to or during contact with the nanoparticle. In embodiments, the reducing agent may be chosen from dithiobutylamine, 2-mercaptoethanol, 2-mercaptoethylamine, tris(2-carboxyethyl) phosphine (TCEP), cysteine, dithiothreitol (DTT), among others. In a preferred embodiment, the reducing agent may be TCEP.

According to another embodiment, the change in the spectrophotometric property of the nanoparticle may be any suitable change that is associated with an off-flavor maple sample; that is, a change that does not occur upon contacting a good taste maple sample. According to an embodiment, such a change may be a change of color, for example a change from red to blue. According to this embodiment, such a visually assessable change may be particularly useful when assessing samples of maple on location, for example at the maple shack, farm or other locations where maple syrup production and transformation is made. According to another embodiment, the change of the spectrophotometric property may be a change in absorbance. For example, the change in absorbance may be an increase in the absorbance of the UV-Vis-NIR spectra. In another embodiment, the increase of absorbance for gold nanoparticles can be in the region of about 400 nm to about 1000 nm. In an embodiment, the change in absorbance may be a differential absorbance between the absorbance at any wavelength superior to the maximum wavelength of absorption of the nanoparticle in absence of buddy samples (i.e. in good flavor maple samples). According to an embodiment, the change in absorbance may be a differential absorbance between a wavelength where absorbance remains stable (i.e. that does not increase or decrease; is unchanged) in any maple sample and another wavelength where a change in absorbance is observed in an off flavor sample. According to an embodiment, the differential absorbance can be selected from ≥561 nm to 1000 nm and absorbance at about ≤560 nm or wavelength below, preferably nearby wavelength below. For example, the wavelength may be any one wavelength between about 490 to about 560 nm, or from about 490 to about 555 nm, or from about 490 to about 550 nm, or from about 490 to about 545 nm, or from about 490 to about 540 nm, or from about 490 to about 535 nm, or from about 490 to about 530 nm, or from about 490 to about 525 nm, or from about 490 to about 520 nm, or from about 490 to about 515 nm, or from about 490 to about 510 nm, or from about 490 to about 505 nm, or from about 490 to about 500 nm, or from about 490 to about 495 nm, or from about 495 to about 500 nm, or from about 500 to about 505 nm, or from about 505 to about 510 nm, or from about 510 to about 515 nm, or from about 515 to about 520 nm, or from about 520 to about 525 nm, or from about 525 to about 530 nm, or from about 530 to about 535 nm, or from about 535 to about 540 nm, or from about 540 to about 545 nm, or from about 545 to about 550 nm, or from about 550 to about 555 nm, or from about 555 to about 560 nm, or from about 550 to about 560 nm, or from about 540 to about 550 nm, or from about 530 to about 540 nm, or from about 520 to about 530 nm, or from about 510 to about 520 nm, or from about 500 to about 510 nm, or about 560, 559, 558, 557, 556, 555, 554, 553, 552, 551, 550, 549, 548, 547, 546, 545, 544, 543, 542, 541, 540, 539, 538, 537, 536, 535, 534, 533, 532, 531, 530, 529, 528, 527, 526, 525, 524, 523, 522, 521, 520, 519, 518, 517, 516, 515, 514, 513, 512, 511, 510, 509, 508, 507, 506, 505, 504, 503, 502, 501, 500, 499, 498, 497, 496, 495, 494, 493, 492, 491 or 490 nm. In another embodiment, the change in absorbance may be a differential absorbance between any one wavelength equal to or greater than 561 nm and any one wavelength equal to or smaller than 560 nm, for example the differential absorbance between absorbance at 610 nm and absorbance at 560 nm, and/or between absorbance at 630 nm and absorbance at 530 nm, and/or between absorbance at 640 nm and absorbance at 520 nm, or any suitable pairing of any one wavelengths at about 560 nm or below and any one wavelength ≥561 nm to 1000 nm. In certain embodiments, a positive differential absorbance will be associated with an off-flavor maple syrup, while a negative differential absorbance is associated with a good flavor maple syrup. According to an embodiment, the change in the spectrophotometric property of the nanoparticle may be both a change of color and of absorbance. In another embodiment, the change in the wavelength of maximum absorption between a (known) good tasting maple sample and a tested maple sample can be tracked and related to off-flavor maple syrup. In an embodiment, in the off-flavor maple sample the wavelength of maximum absorption would be displaced to a higher wavelength than in a good tasting maple sample.

According to another embodiment, the maple sample tested in the method of the present invention may be a diluted maple syrup sample or a pure maple syrup sample, a pure sap sample or a diluted sap sample, a pure sap concentrate sample, or a diluted sap concentrate sample. For example, the diluted maple syrup, sap or sap concentrate may be undiluted or diluted from about 1:1 to 1:1000 in a solvent. Products on the market may be manufactured from off-flavor maple syrups, maple saps, and maple sap concentrates in their diluted forms, and such maple samples are encompassed as maples samples. According to an embodiment, the solvent may be water or organic solvents, for example ultrapure or distilled water or other grades of water.

According to another embodiment, the concentration (or amount) of the spherical nanoparticle is in the method of the present invention may be from about 0.1 nM to about 100 nM, or from about 0.1 nM to about 90 nM, or from about 0.1 nM to about 80 nM, or from about 0.1 nM to about 70 nM, or from about 0.1 nM to about 60 nM, or from about 0.1 nM to about 50 nM, or from about 0.1 nM to about 40 nM, or from about 0.1 nM to about 30 nM, or from about 0.1 nM to about 25 nM, or from about 0.1 nM to about 20 nM, or from about 0.1 nM to about 15 nM, or from about 0.1 nM to about 10 nM, or from about 0.1 nM to about 5 nM, or from about 0.1 nM to about 2 nM, or from about 0.1 nM to about 1 nM, or from about 1 nM to about 100 nM, or from about 1 nM to about 90 nM, or from about 1 nM to about 80 nM, or from about 1 nM to about 70 nM, or from about 1 nM to about 60 nM, or from about 1 nM to about 50 nM, or from about 1 nM to about 40 nM, or from about 1 nM to about 30 nM, or from about 1 nM to about 25 nM, or from about 1 nM to about 20 nM, or from about 1 nM to about 15 nM, or from about 1 nM to about 10 nM, or from about 1 nM to about 5 nM, or from about 1 nM to about 2 nM, or from about 2 nM to about 100 nM, or from about 2 nM to about 90 nM, or from about 2 nM to about 80 nM, or from about 2 nM to about 70 nM, or from about 2 nM to about 60 nM, or from about 2 nM to about 50 nM, or from about 2 nM to about 40 nM, or from about 2 nM to about 30 nM, or from about 2 nM to about 25 nM, or from about 2 nM to about 20 nM, or from about 2 nM to about 15 nM, or from about 2 nM to about 10 nM, or from about 2 nM to about 5 nM, or from about 5 nM to about 100 nM, or from about 5 nM to about 90 nM, or from about 5 nM to about 80 nM, or from about 5 nM to about 70 nM, or from about 5 nM to about 60 nM, or from about 5 nM to about 50 nM, or from about 5 nM to about 40 nM, or from about 5 nM to about 30 nM, or from about 5 nM to about 25 nM, or from about 5 nM to about 20 nM, or from about 5 nM to about 15 nM, or from about 5 nM to about 10 nM, or from about 10 nM to about 100 nM, or from about 10 nM to about 90 nM, or from about 10 nM to about 80 nM, or from about 10 nM to about 70 nM, or from about 10 nM to about 60 nM, or from about 10 nM to about 50 nM, or from about 10 nM to about 40 nM, or from about 10 nM to about 30 nM, or from about 10 nM to about 25 nM, or from about 10 nM to about 20 nM, or from about 10 nM to about 15 nM, or from about 20 nM to about 100 nM, or from about 20 nM to about 90 nM, or from about 20 nM to about 80 nM, or from about 20 nM to about 70 nM, or from about 20 nM to about 60 nM, or from about 20 nM to about 50 nM, or from about 20 nM to about 40 nM, or from about 20 nM to about 30 nM, or from about 20 nM to about 25 nM, or from about 25 nM to about 100 nM, or from about 25 nM to about 90 nM, or from about 25 nM to about 80 nM, or from about 25 nM to about 70 nM, or from about 25 nM to about 60 nM, or from about 25 nM to about 50 nM, or from about 25 nM to about 40 nM, or from about 25 nM to about 30 nM, or from about 30 nM to about 100 nM, or from about 30 nM to about 90 nM, or from about 30 nM to about 80 nM, or from about 30 nM to about 70 nM, or from about 30 nM to about 60 nM, or from about 30 nM to about 50 nM, or from about 30 nM to about 40 nM, or from about 40 nM to about 100 nM, or from about 40 nM to about 90 nM, or from about 40 nM to about 80 nM, or from about 40 nM to about 70 nM, or from about 40 nM to about 60 nM, or from about 40 nM to about 50 nM, or from about 50 nM to about 100 nM, or from about 50 nM to about 90 nM, or from about 50 nM to about 80 nM, or from about 50 nM to about 70 nM, or from about 50 nM to about 60 nM, or from about 60 nM to about 100 nM, or from about 60 nM to about 90 nM, or from about 60 nM to about 80 nM, or from about 60 nM to about 70 nM, or from about 70 nM to about 100 nM, or from about 70 nM to about 90 nM, or from about 70 nM to about 80 nM, or from about 80 nM to about 100 nM, or from about 80 nM to about 90 nM, or from about 90 nM to about 100 nM, or 0.1, 1, 2, 3, 4, 5, 10, 15, 20, 25, 30, 40, 50, 60, 70, 80, 90, 100 nM of nanoparticles.

According to another embodiment, the contact between the nanoparticles and the maple sample tested may be from a few seconds, to a few minutes, dependent upon the concentration of the sample, but importantly, the amount of compounds causing the taste defect present therein. For example, the contact may be about 1, 5, 10, 20, 30, 40, 50, 60 seconds, or about 1 minute to about 60 minutes, or about 1 minute to about 55 minutes, or about 1 minute to about 50 minutes, or about 1 minute to about 45 minutes, or about 1 minute to about 40 minutes, or about 1 minute to about 35 minutes, or about 1 minute to about 30 minutes, or about 1 minute to about 25 minutes, or about 1 minute to about 20 minutes, or about 1 minute to about 15 minutes, or about 1 minute to about 10 minutes, or about 1 min to about 5 minutes.

The present invention will be more readily understood by referring to the following examples which are given to illustrate the invention rather than to limit its scope.

EXAMPLE 1

Synthesis of Nanoparticles

Initial analysis noted that dimethyldisulfide (DMDS) is present in buddy maple syrups. It is a smelly compound with a very unpleasant garlic odor. Because of the chemical composition of DMDS, an aggregation test of gold nanoparticles was envisioned. To validate this test, the analysis of a dozen good taste maple syrup samples with a simulated buddy taste defect was necessary in order to create a reference for the colorimetric test. Maple syrup with a buddy taste is classified as a buddy syrup or VR5 in the industry.

Gold Nanoparticles

Maple syrup consists of 66% w/w carbohydrates (where 96% is sucrose) and 33% water, and the remaining 1% is composed of organic and inorganic molecules, i.e. organic acids, minerals, nitrogenous and phenolic compounds as well as several other trace elements. Gold nanoparticles (AuNPs) were selected since they do not react with the main compounds of maple syrup. While they have a high affinity with sulfur compounds like DMDS, they will form a gold-sulfur bond (Au—S) causing a destabilization of gold colloids and causing their aggregation. In addition, AuNPs change color depending on whether they are free or linked with the DMDS. Different types and sizes of gold nanoparticles have been used to maximize their affinity with DMDS.

To synthesize nanoparticles, it is important to wash all the glassware and the magnetic bar in aqua regia, i.e. 3 parts of concentrated HCl for 1 part concentrated $HNO_3$, and then rinse thoroughly with distilled water (18-MΩ) to remove all traces of acid. Subsequently, there are three protocols depending on the type of desired nanoparticles: spherical-, star- and raspberry-shaped. For spherical AuNPs two solutions are prepared; (1) 68 mg $HAuCl_4$ in 200 mL of ultrapure water and (2) 200 mg of sodium citrate dihydrate in 20 mL of ultrapure water. The solution (1) is heated to boiling with vigorous stirring. The solution (2) is then added and is heated and stirred for 10 minutes and then left to rest at room temperature. The solution is of a blood red color.

For the synthesis of star-shaped AuNPs, two solutions are prepared; (1) $HAuCl_4$ (250 mM) in ultrapure water and (2) HEPES (4-(2-hydroxyethyl)-1-piperazine ethanesulfonic acid) at 100 mM in 40 mL of ultrapure water at pH 7.4. 80 µL of the solution (1) is added to 100 mL of ultrapure water and is stirred at room temperature. Solution (2) is then added and stirred for a few seconds until the reagents are thoroughly mixed. The solution is then left to rest, without stirring, at room temperature for two hours. The suspension gradually turns to turquoise blue.

For the synthesis of raspberry-shaped AuNPs two solutions are prepared; (1) $HAuCl_4$ (250 mM) in ultrapure water and (2) HEPES (100 mM) in 10 mL of ultrapure water at pH 7.4. Three ml of the solution (2) are added to 100 mL of ultrapure water and are stirred at room temperature. Then, 100 µL of the solution (1) is added dropwise with stirring for two hours. The solution turns from pale yellow to colorless, then gradually to blue in transmission.

To concentrate the colloidal suspensions, they are centrifuged at 10,000 RPM for 5 minutes. After centrifugation, the supernatant is removed and the fractions are combined and thoroughly shaken in an ultrasonic bath. All nanoparticles are refrigerated at 4° C. until use.

To increase the size of the AuNPs, two solutions are prepared; (1) 51 mg $HAuCl_4$ in 600 mL of ultrapure water (250 mM) and (2) 700 mg of $NH_2OH$ in 50 mL of ultrapure water. 15 mL of the AuNPs solution is added in 400 mL of ultrapure water, then 3 mL of the solution (2) is added. Then, 500 µL of the solution (1) is added dropwise with stirring for 10 minutes.

EXAMPLE 2

Selection of Nanoparticles

The selection of the type of gold nanoparticles to react with DMDS was determined using preliminary tests. To do this, three types of AuNPs (raspberry-, star- and spherical-shaped) were added to a good taste syrup diluted 10 times in water. This dilution enables the reduction of the sugar level (° Brix) and helps visualizing the aggregation of the nanoparticles. Only spherical AuNPs will remain stable for a period of at least 30 minutes. Indeed, FIG. 1 shows the stability of spherical AuNPs after 50 minutes in a diluted maple syrup sample. Stability is indicated by a lack of change in the UV-Vis spectrum (wavelength 400 nm to 850 nm is illustrated) of these nanoparticles in the presence of diluted maple syrup. The star-shaped and raspberry-shaped AuNPs cannot be used in this type of analysis because they react significantly in a syrup having a "good taste", in the absence of any DMDS, and noted by an increase of the absorbance at wavelengths above 520 nm. In addition, for the purposes of this experiment, it is important to have a significant color change of AuNPs when in the presence of DMDS. The size of about 15 nm of spherical AuNPs is a suitable choice, because the smaller the nanoparticles, the lower the concentration of DMDS necessary to aggregate them.

EXAMPLE 3

Interactions Between DMDS Doped Maple Syrup and Spherical AuNPs

Figure 2:
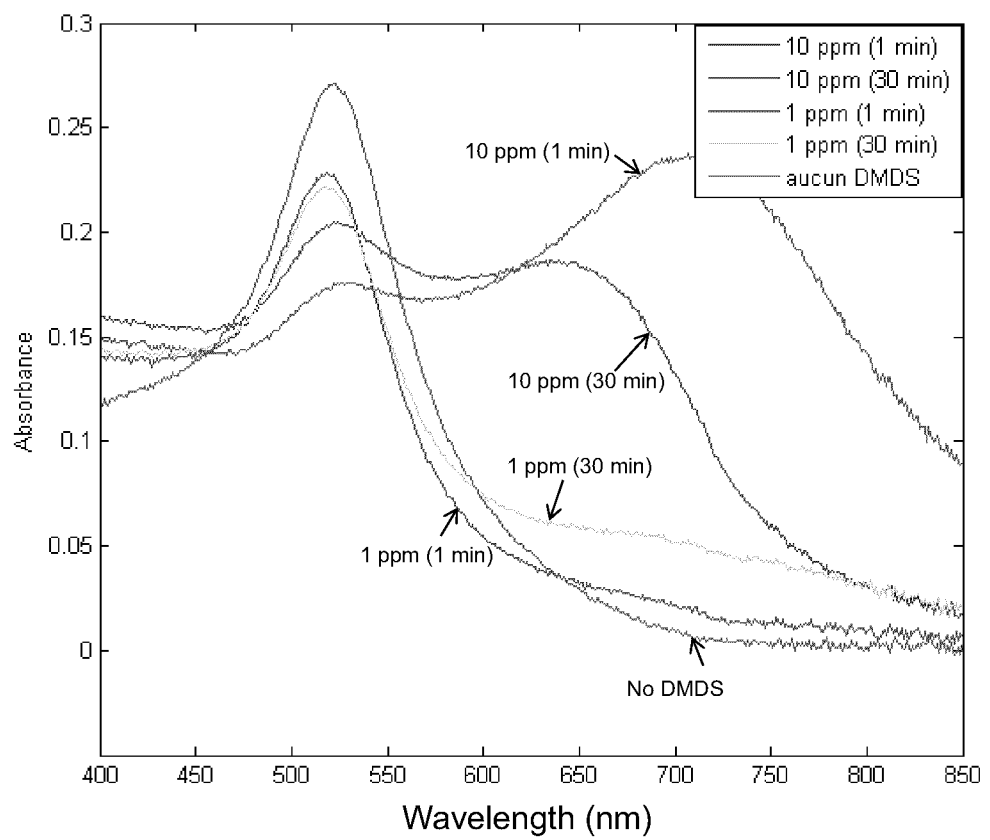
FIG. 2 illustrates the extinction spectra (UV-Vis) of spherical AuNPs after addition of 1 mg/L and 10 mg/L of DMDS at 1 minute and 30 minutes reaction time.

Now referring to FIG. 2, 1 mL spherical AuNPs are introduced into 1 mL DMDS-doped maple syrups (syrup diluted 10 times in water). At very high concentrations—in the order of mg/L—the spherical AuNPs react very quickly and it is possible to visually observe a color change of the solution which changes from red to blue. This color change is caused by the aggregation of AuNPs, due to the adsorption of DMDS molecules on their surface, thus decreasing their zeta potential. The zeta potential determines, among other things, the stability of the colloids. However, when working with DMDS concentrations in the order of µg/L, such a change is no longer observable with the naked eye. Indeed, even at 1 mg/L (1000 ppb), use of a spectrophotometer is necessary to see the change in absorbance (FIG. 2).

EXAMPLE 4

Treatment with a Reducing Agent

To increase sensitivity of the method of the present invention, a reducing agent was added to the samples in order to facilitate adsorption of DMDS to AuNPs. According to an embodiment, tris (2-carboxyethyl) phosphine (TCEP) was selected as such a suitable reducing agent. TCEP is often used as a reducing agent to break disulfide bonds. Thus, by breaking the disulfide bond of the DMDS, the resulting product will be methylsulfide which will allow it to be more easily adsorbed on the surface of the AuNPs by dislodging the citrate molecules. To better understand the effects of TCEP addition, a Surface Plasmon Resonance (SPR) detection system was used to measure the variation of the refractive index in the vicinity of the interface when the DMDS binds to a gold surface. SPR is a more sensitive system than gold nanoparticles. Using SPR the affinity between DMDS and a gold surface with and without the presence of TCEP was determined (FIGS. 3 and 4).

Figure 3:
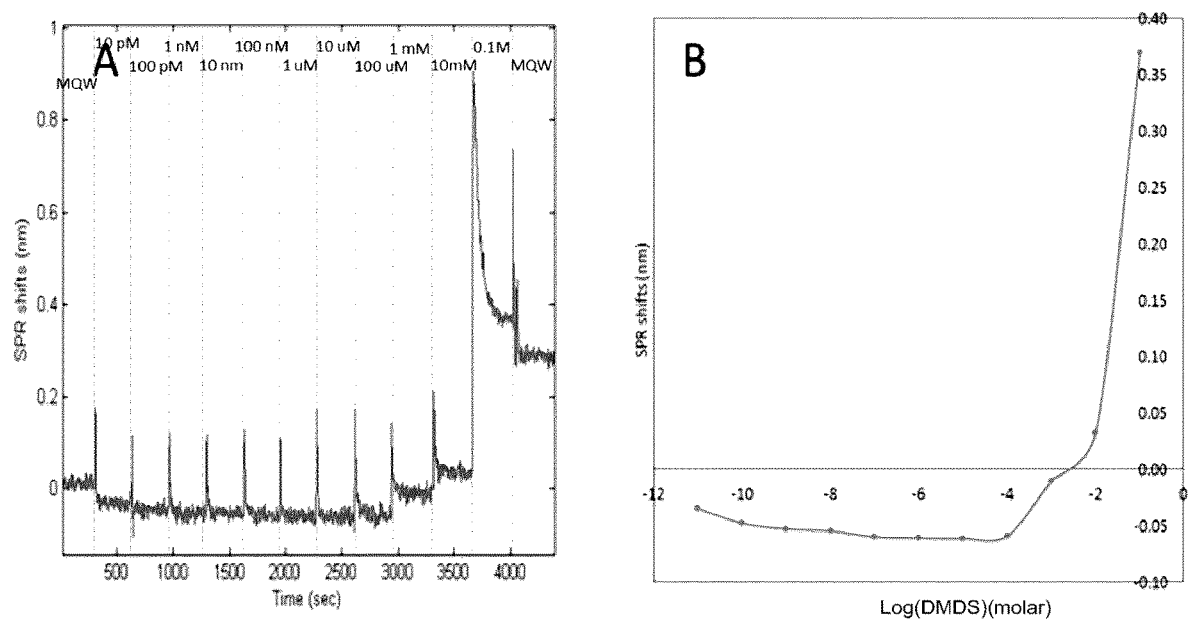
FIG. 3A illustrates a sensorgram for the binding of DMDS in ultrapure water.
FIG. 3B illustrates a calibration curve for the binding of DMDS in ultrapure water.
Figure 4:
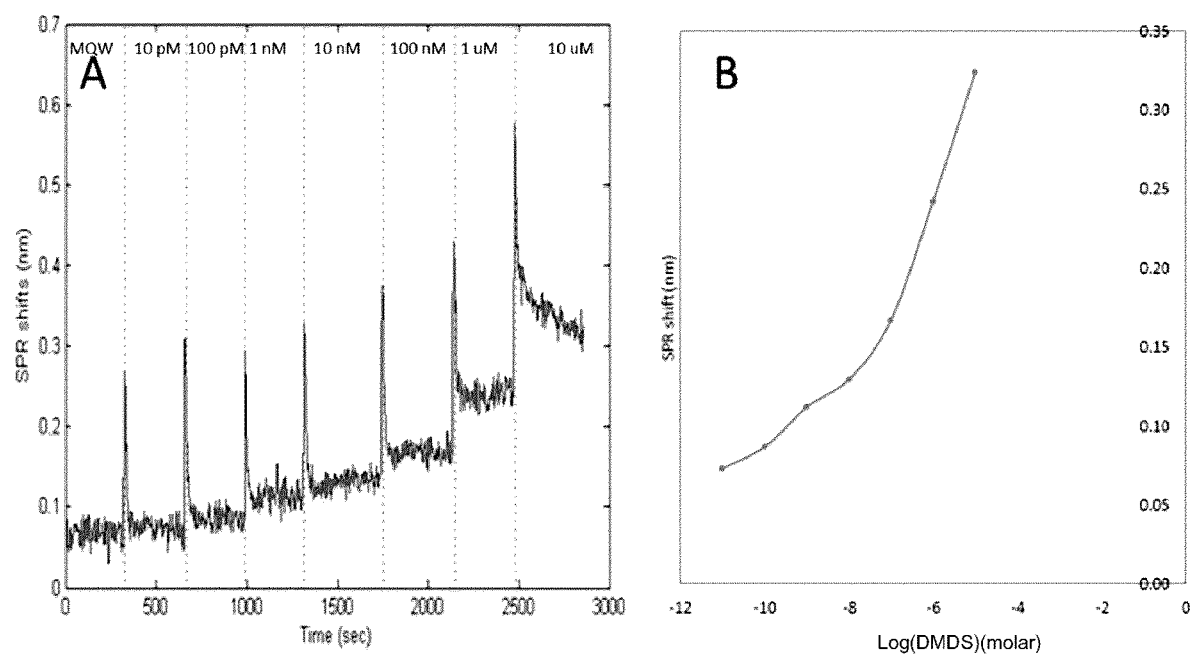
FIG. 4A illustrates a sensorgram for the binding of DMDS in ultrapure water in the presence of an excess of TCEP (3.5 mM).
FIG. 4B illustrates a calibration curve for the binding of DMDS in ultrapure water in the presence of an excess of TCEP (3.5 mM).

According to FIGS. 3 and 4, the addition of TCEP greatly improves the adsorption of DMDS by showing a larger SPR signal at low concentrations. Without the presence of TCEP the concentration of DMDS must be in the order of mmol/L to detect an interaction with the gold layer. However, in the presence of TCEP, it is possible to see an interaction with a DMDS concentration in the order of pmol/L (<1 ppb). Thus, with TCEP, it is possible to measure low concentrations of DMDS by analyzing the shoulder of UV-vis spectra with AuNPs.

Figure 5:
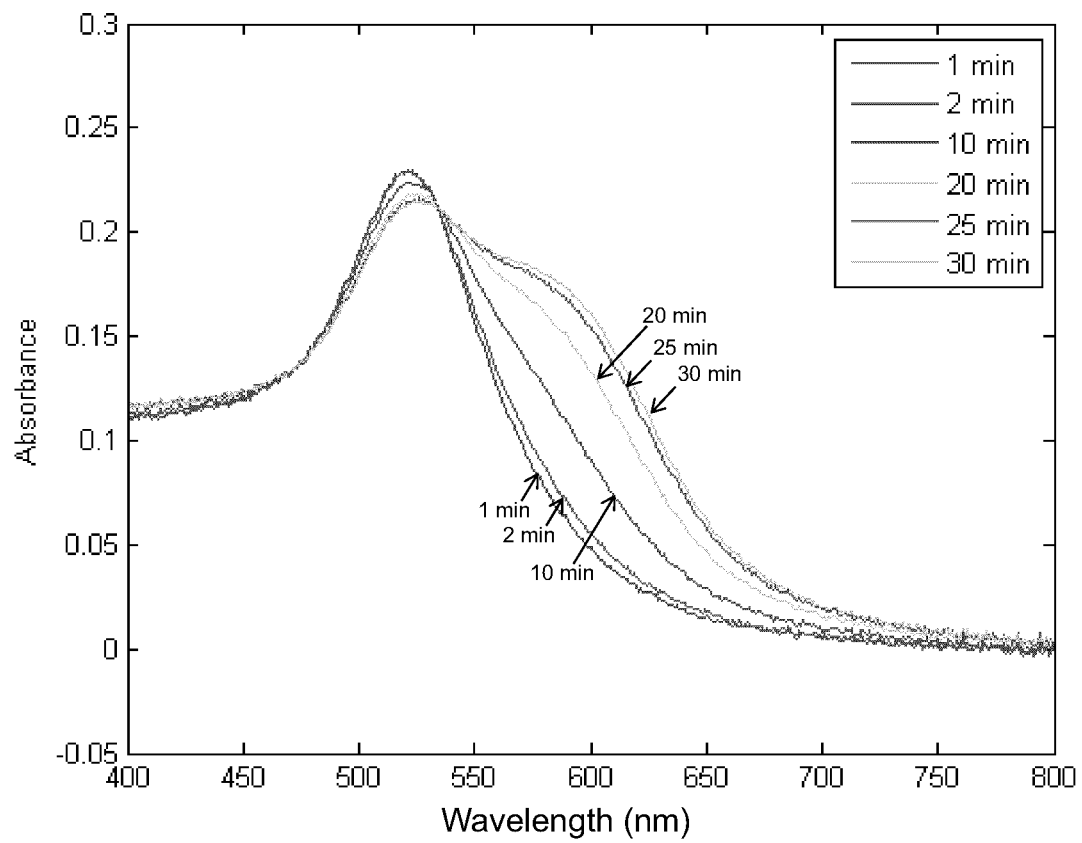
FIG. 5 illustrates the extinction spectra (UV-vis) spherical AuNPs after addition of 40 µg/L of DMDS and excess (16 µM) of TCEP in 10-fold diluted maple syrup.

Next, good taste maple syrups samples were spiked with DMDS and TCEP to the DMDS-containing maple syrup samples. The maple syrup samples were diluted 10 times in ultrapure water, and an excess of TCEP (16 µM) was used. FIG. 5 shows that a detection limit of 40 µg/L is achieved. This dilution is optimal because the ° Brix is about 6 which helps the homogenization of maple syrup samples and nanoparticles, and eliminates the need to acquire a blank for each maple syrup sample. It is also possible to work with a ° Brix up to 1, but at such a dilution it becomes difficult to detect the aggregation of AuNPs.

EXAMPLE 5

Testing of Maple Syrup Samples

Figure 6:
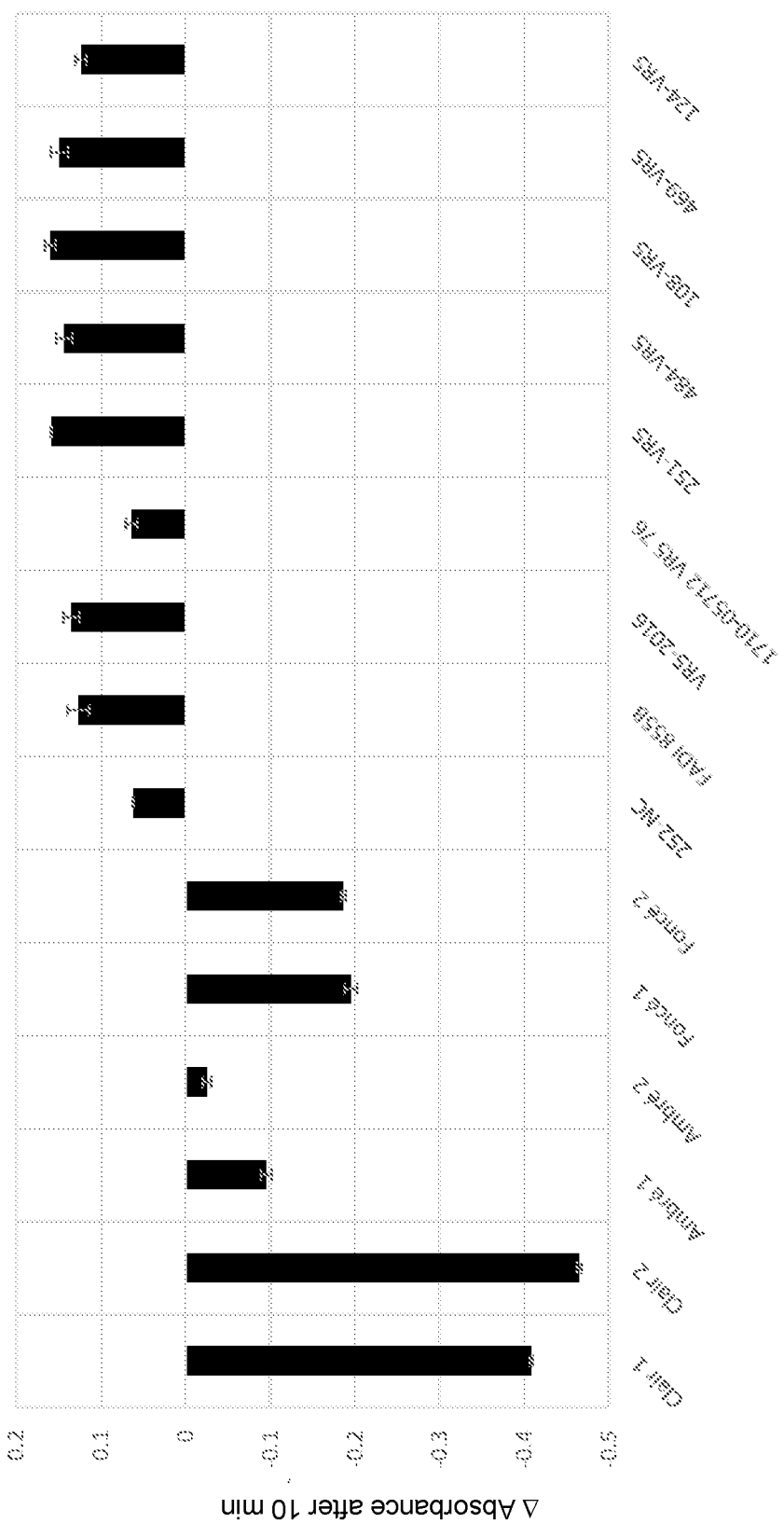
FIG. 6 illustrates the differential absorbance between wavelengths 610 nm and 520 nm of the AuNPs (n=3 for each sample).

Next, good tasting maple syrup samples (2 clear syrups, 2 amber syrups and 2 dark syrups) and a series of buddy taste maple syrup samples [9 buddy (VR5) syrups] were analyzed by the above described technique to classify these samples. 1 mL of AuNP were reacted with 1 mL of syrup samples diluted 10 times in water. To achieve this, the difference in absorbance between two wavelengths—610 nm and 520 nm—is measured. A negative value is indicative of the absence of aggregation of AuNPs and indicates a negative test, or in other words, that the maple syrup sample is a good flavor maple syrup. However, a positive value is a suggestion of the presence of molecules reacting with AuNPs in the sample and indicates a positive test, or in other words that the maple syrup sample is an off-flavor [e.g. buddy (VR5)] maple syrup. Now referring to FIG. 6, it is shown that the good tasting samples all scored negative values in our test and all the buddy (VR5) samples all scored positive values. The analysis solution is of a red hue for the negative values and blue hue for the positive ones. In addition, rapid aggregation (a few seconds) of AuNPs was observed for off-flavor buddy (VR5) syrups. Based on the results obtained, concentrations well above 40 µg/L for DMDS would be expected in the off-flavor syrups due to the almost instantaneous color change of AuNPs, while a DMDS standard at 40 µg/L did not cause a significant color change in AuNPs (negative value) according to FIG. 6.

EXAMPLE 6

Correlation of DMDS Content with Off-Flavor of Maple Syrup Sample

To determine if the off-flavor samples contained a high concentration of DMDS, an analysis for the amount of this molecule in buddy maple syrup was carried out by SPME-GC/MS (Table 1).

TABLE 1

SPME-GC/MS analysis of the DMDS content of buddy (VR5) maple syrup samples (LQ: 3.4 ppb)

| Sample code | DMDS concentration (ppb) |
| --- | --- |
| 252-NC | <LQ |
| FADI 855B | 50.4 |
| VR5-2016 | 266.8 |
| 1710-05712 VR5 76 | 11.6 |
| 251-VR5 | 61.4 |
| 484-VR5 | 45.1 |
| 108-VR5 | 18.7 |
| 469-VR5 | 31.2 |
| 124-VR5 | 36.2 |
| 324-FO-VR5 | 75.2 |
| FO 427-VR5 | 225.8 |

Figure 7:
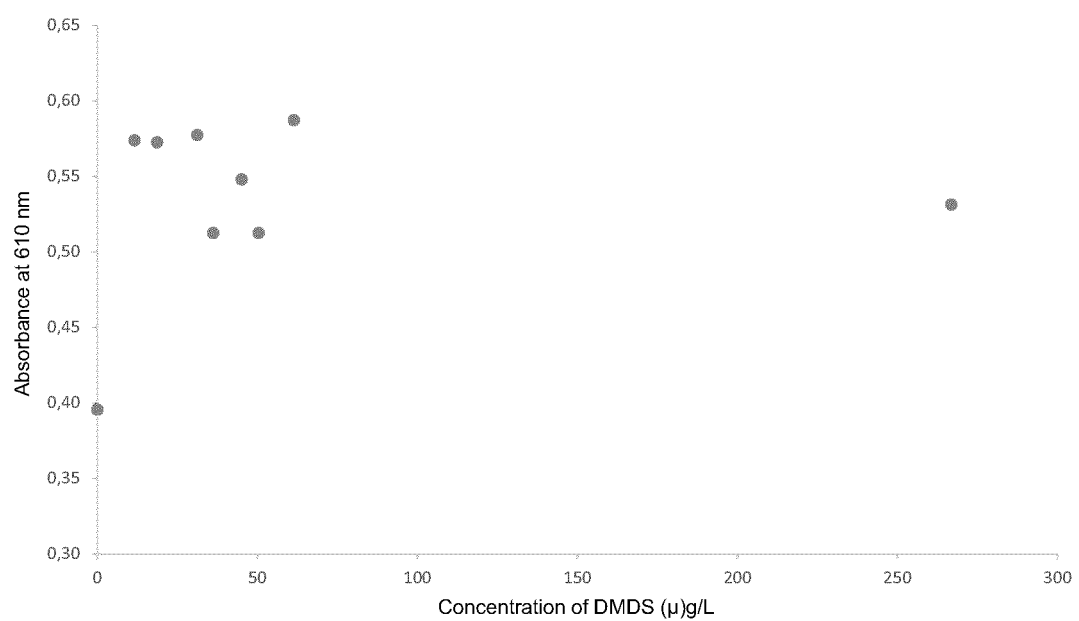
FIG. 7 illustrates the absorption of spherical AuNPs at 610 nm after 10 minutes at different concentrations of DMDS in buddy (VR5) maple syrups.
Figure 8:
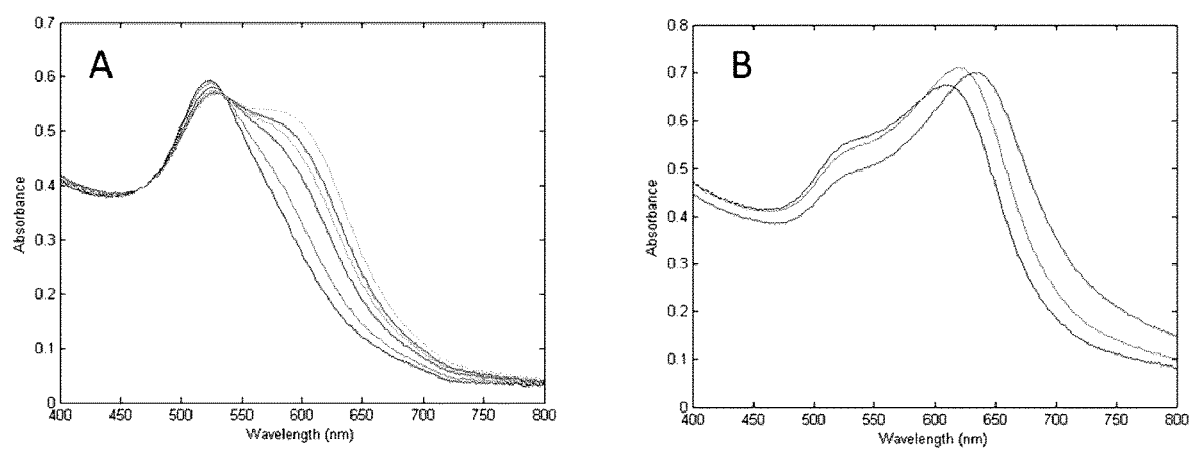
FIG. 8A illustrates the UV-Vis spectrum of spherical AuNPs after addition of 500 µg/L of DMDS in 10-fold diluted maple syrup (good tasting).
FIG. 8B illustrates the UV-Vis spectrum of spherical AuNPs containing 18.7 µg/L of DMDS in 10-fold diluted maple syrup (buddy (VR5) maple syrup).

The results show DMDS concentrations between 0 and 200 ppb with a limit of quantification (LOQ) of 3.4 ppb. No correlation is observed between the concentration of DMDS and the result of the AuNP test (FIG. 7). If DMDS was the sole contributor to the classification test for off-flavor maple syrup samples, a progressive increase in AuNP absorbance at 610 nm with increasing concentration of DMDS would have been expected. However, the maple syrup samples containing no DMDS were still classified as buddy syrup (VR5) by an independent analysis and by the method of the present invention. This suggests that the molecular complexity of off-flavor [e.g. buddy (VR5)] maple syrups exceeds the mere presence of DMDS. In preliminary tests with DMDS spiking of maples syrups to cause aggregation equivalent to that of all measured buddy (VR5) syrups, it is estimated that a DMDS concentration of approximately 1 ppm (mg/L) would be required. FIGS. 8A and 8B clearly demonstrates this result, where the UV-Vis spectrum of spherical AuNPs in (A) a syrup with good taste doped with 500 µg/L of DMDS underwent a smaller response of the absorbance maximum than (B) a buddy (VR5) syrup containing 18.7 µg/L of DMDS. This shows that DMDS is not the only potential cause of the off-flavor of the buddy (VR5) maple syrup samples.

Figure 9:
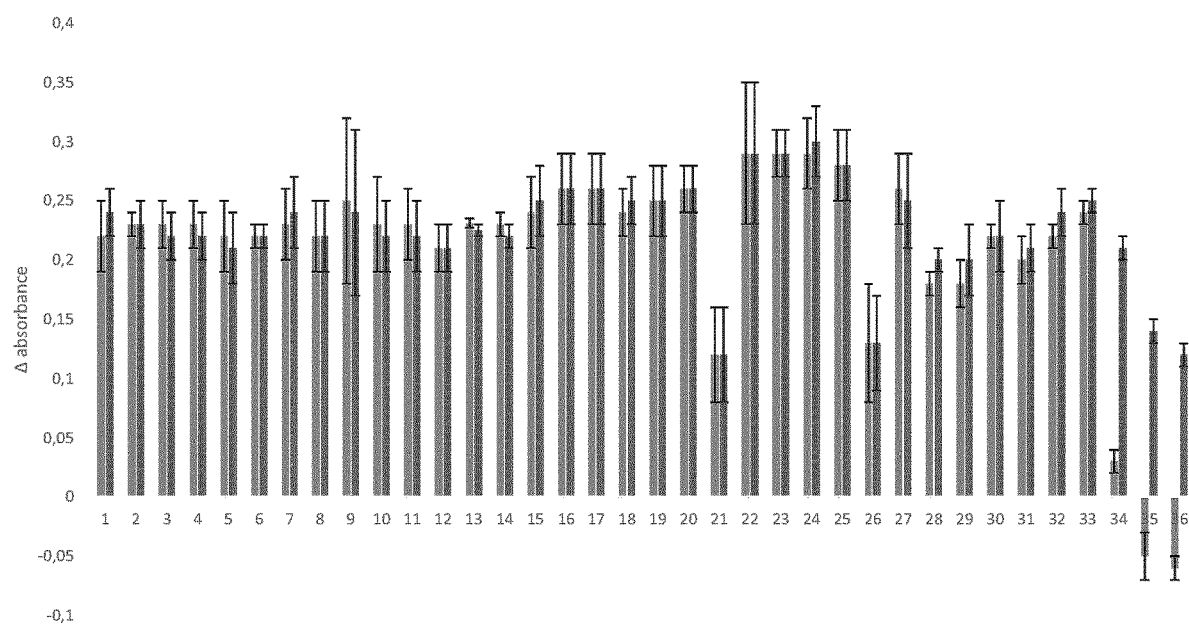
FIG. 9 illustrates test results of different maple syrups (n=3) (The absorbance was calculated between 630 nm and 520 nm after 1 minute (blue) and between 640 nm and 520 nm after 10 minutes (orange).) The sample numbers correspond to those provided by the FPAQ in February 2018.
Figure 10:
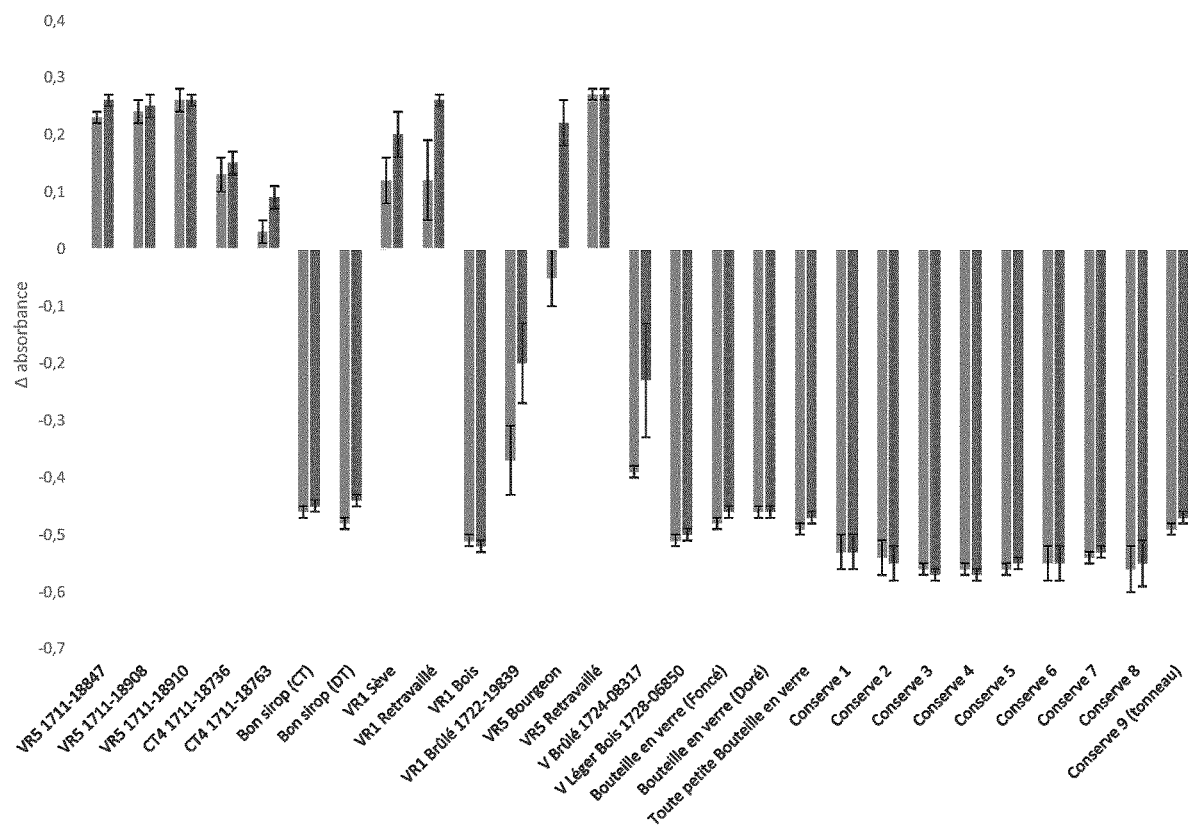
FIG. 10 illustrates test results of different maple syrups (n=3) (The absorbance was calculated between 630 nm and 520 nm after 1 minute (blue) and between 640 nm and 520 nm after 10 minutes (orange).) The sample numbers correspond to those provided by the FPAQ in February 2018.

To increase confidence in the results of the maple syrup grading method described above, an additional 63 maple syrup samples were evaluated, including light, amber, dark, very dark, and buddy (VR5) samples (FIGS. 9 and 10). Of the 63 samples, 36 were blind tested (FIG. 9). The good tasting samples all have a negative value with the method of the present invention and the buddy (VR5) samples all have a positive value. In addition, rapid aggregation (a few seconds) of AuNPs was obtained for buddy (VR5) maple syrup samples. According to an embodiment of the present invention, it is important to measure the difference in absorbance between the wavelengths of 630 nm and 520 nm after 1 minute of AuNPs injection and between 640 nm and 520 nm after 10 minutes. Even if the color change of the solution is almost instantaneous, taking a UV-vis spectrum offers a more objective measurement while the color change is more subjective.

To validate these results, a DMDS analysis of syrups 1 to 36 from FIG. 9 by SPME-GC/MS was carried out (Table 2).

TABLE 2

Study on reworked syrup samples and comparison of classification results and DMDS (SPME-GC-MS analysis to determine DMDS content).

| Sample | Barrel sequence | Code FPAQ 1714- | ACER Classif. | FPAQ Classif. | DMDS Real ppb |
| --- | --- | --- | --- | --- | --- |
| 1 | 169 | 14148 | VR4 | VR5 | 35.3 |
| 2 | 167 | 14227 | VR4 | VR5 | 24.5 |
| 3 | 163 | 14236 | VR5 | VR5 | 110.9 |
| 4 | 161 | 14153 | VR4 | VR5 | 35.5 |
| 5 | 160 | 14224 | VR5 | VR5 | 59.5 |
| 6 | 155 | 14120 | VR4 | VR5 | 37.2 |
| 7 | 153 | 14108 | VR4 | VR5 | 90.3 |
| 8 | 151 | 14113 | VR2 | VR5 | 58.3 |
| 9 | 123 | 14113 | VR1 | VR5 | 45.5 |
| 10 | 143 | 14235 | VR5 | VR5 | 57.3 |
| 11 | 131 | 14253 | VR1 | VR5 | 47.1 |
| 12 | 141 | 14153 | NC2 | VR5 | 14.7 |
| 13 | 135 | 14207 | VR2 | VR5 | 49.9 |
| 14 | 136 | 14039 | VR1 | VR4 | 5 |
| 15 | 102 | 14128 | NC4 | VR4 | 7.1 |
| 16 | 105 | 14241 | VR1 | VR5 | 30 |
| 17 | 104 | 14214 | VR2 | VR5 | 68.7 |
| 18 | 98 | 14256 | NC4 | VR5 | 36 |
| 19 | 108 | 14251 | VR2 | VR5 | 72 |
| 20 | 109 | 14255 | VR2 | VR5 | 53 |
| 21 | 96 | 14250 | NC4 | VR5 | 22.9 |
| 22 | 106 | 14262 | VR1 | VR5 | 45.8 |
| 23 | 112 | 14264 | VR5 | VR5 | 51.5 |
| 24 | 116 | 14111 | VR1 | VR5 | 34 |
| 25 | 119 | 14115 | VR5 | VR5 | 53.7 |
| 26 | 75 | 14150 | NC4 | VR5 | 12.2 |
| 27 | 73 | 14181 | NC4 | VR5 | 31.7 |
| 28 | 69 | 14129 | NC2 | VR4 | 4.9 |
| 29 | 66 | 14138 | NC2 | VR5 | 13.7 |
| 30 | 67 | 14135 | NC2 | VR5 | 14.7 |
| 31 | 36 | 14133 | NC2 | VR5 | 14.1 |
| 32 | 41 | 14099 | BON GOUT | VR4 | 4.2 |
| 33 | 42 | 14097 | BON GOUT | VR4 | 4.4 |
| 34 | 43 | 14093 | BON GOUT | BON GOUT | <3.4 |
| 35 | 44 | 14085 | BON GOUT | BON GOUT | <3.4 |
| 36 | 45 | 14087 | BON GOUT | BON GOUT | <3.4 |

Figure 11:
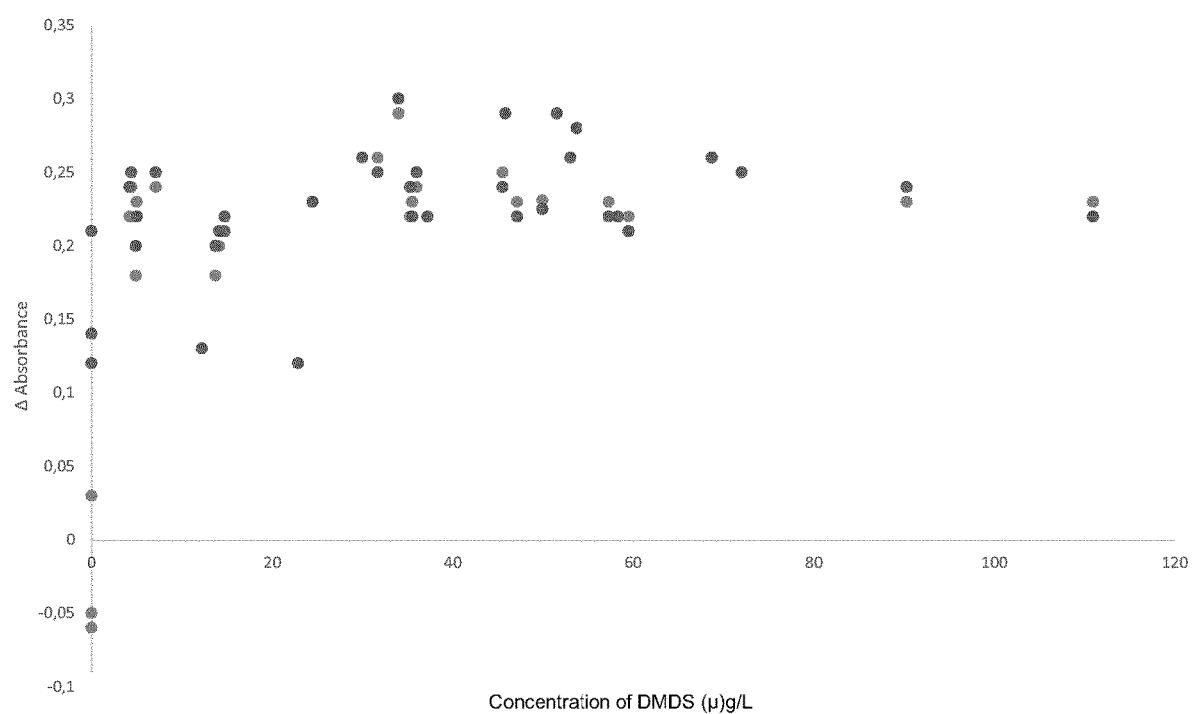
FIG. 11 illustrates the absorption difference of the spherical AuNPs at 610 nm after 10 minutes at different concentrations of DMDS in maple syrup (The absorbance was calculated between 630 nm and 520 nm after 1 minute (blue) and between 640 nm and 520 nm after 10 minutes (orange)).

The results showed DMDS concentrations between 0 and 150 ppb with a limit of quantification (LOQ) of 3.4 ppb. Thus, the correlation was not revealed between the concentration of DMDS and the result of our test (FIG. 11). This reinforces the hypothesis that the molecular complexity of VR5 syrups exceeds the mere presence of DMDS.

The method of the present invention elaborates on an effective method to differentiate a maple syrup (and sap) with good taste from a maple syrup with an off-flavor (e.g. buddy (VR5)) with good sensitivity and specificity. This is true even though there is no correlation between the concentration of DMDS in the samples and the test result. The off-flavor of the buddy (VR5) maple syrup samples appears to be caused by a more complex phenomenon than anticipated, and it also appears that the method of the present invention measures a greater range of off-flavor causing molecules than only DMDS.

EXAMPLE 7

Identification of Off-Flavor Causing Compounds of Maple Syrup Samples

The present example is the qualitative analysis of industrial grade maple syrup or sap (e.g. off-flavor maple syrup or sap) to identify compounds that will enhance the commercialization of maple syrup.

Figure 12:
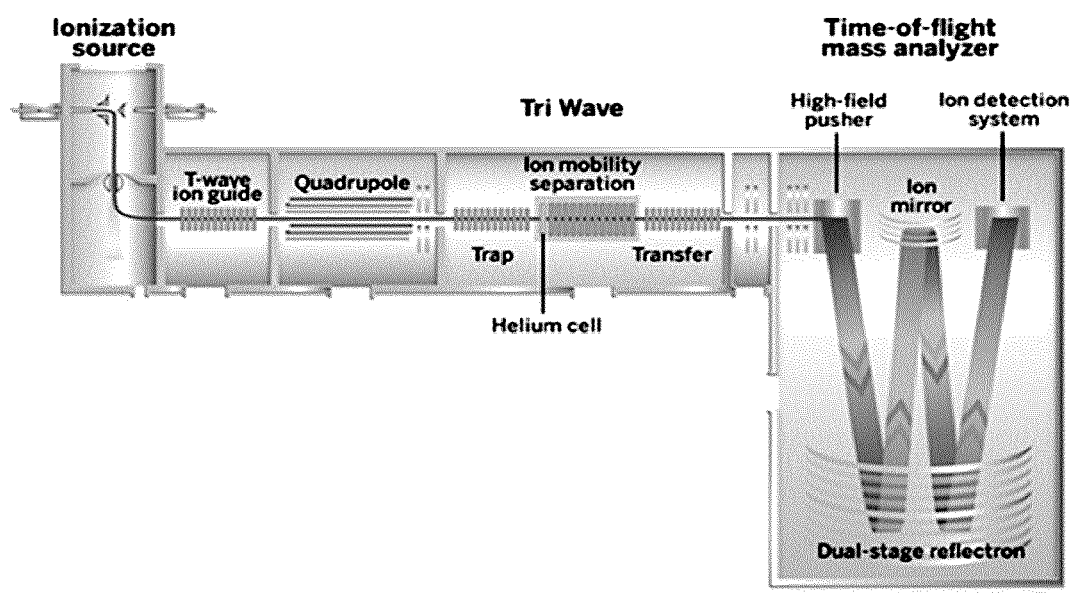
FIG. 12 illustrates a diagrammatic representation of a QTOF Waters Synapt G2-Si Device.

UPLC-TOF Analysis of Maple Syrup
Development of Methods of Extraction and Analysis of Maple Syrup Maple syrup contains on average 66.6% of carbohydrates, 96% of which is sucrose. In order to identify molecules specific to off-flavor maple syrup, a major part of these carbohydrates should be eliminated since sugar solutions cannot be injected in mass spectrometry without severely affecting the performance of the instruments. Different methodologies have therefore been developed by solid phase extraction, SPE. For this purpose, 0.5 mL samples of maple syrup were first diluted with ultrapure water to a final volume of 2.5 mL to decrease the viscosity of the solution applied to the SPE cartridge. Cartridges of different types were used, with a rinsing and elution protocol specific to each, the passage of solvents was obtained by gravity only
Waters Oasis HLB, Cartridge 3 cm$^3$, 60 mg Stationary Phase:
  Wetting: 6 mL of methanol
  Conditioning: 9 mL of water
  Addition of the sample
  Wash: 9 mL of water
  Water removal: Vacuum drawing 10 seconds
  Elution: 1.8 mL of methanol
Waters Oasis WCX, Cartridge 3 cm$^3$, 60 mg Stationary Phase:
  Wetting: 6 mL of methanol
  Conditioning: 9 mL of water
  Addition of the sample
  Wash: 9 mL of water
  Water removal: Vacuum drawing 10 seconds
  Elution: 1.8 mL of 2% HCOOH (v/v) in methanol
Waters Oasis MCX, 3 cc Cartridge, 60 mg Stationary Phase:
  Wetting: 6 mL of methanol
  Conditioning: 9 mL of water
  Addition of the sample
  Wash: 9 mL of water+2% (v/v) HCOOH
  Water removal: Vacuum drawing 10 seconds
  Elution: 1.8 mL of 5% NH$_4$OH (v/v) in methanol An analytical method to obtain optimal separation of organic compounds present in maple syrup extracts was developed in UPLC, coupled with time-of-flight mass spectrometry detection, TOF, with the Waters Synapt G2-Si instrument, shown in FIG. 12. The chromatographic separation was developed with a Waters HSS T3 column with particles 1.8 µm in diameter. The analyzes were conducted with the MSe function, where the fragmentation cell "Transfer" (see FIG. 12) operated in rapid alternation with low and high collision energies. Thus, two chromatograms are obtained in a single measurement, one where the non-fragmented molecules are observed and the other where the fragmentation pattern can be used in order to deduce the molecular structure of the compounds.

The method developed is as follows:
Column: Waters HSS T3, 2.1×150 mm, particles 1.8 µm, 40° C. Flow rate: 0.4 mL/min. Eluent A: H$_2$O+0.1% HCOOH Eluent B: ACN+0.1% HCOOH. Gradient:

TABLE 3 gradient information.

| Time (min.) | % A | % B |
|---|---|---|
| 0 | 95 | 5 |
| 2 | 95 | 5 |
| 15 | 0 | 100 |
| 18 | 0 | 100 |
| 19 | 95 | 5 |
| 30 | 95 | 5 |

The TOF mass spectrometer is always calibrated the day of the analysis sequence, as is the LockSpray ensuring the accuracy of the measured mass/load ratios. The molecule used for the LockSpray is the peptide "leucine encephalin", [M+H]+=556.2771 Da in positive ionization.

Parameters of Mass Spectrometry:
Ionization in positive electrospray, capillary at 2.75 kV, Resolution mode, R≈30 000. Source: 120° C., N$_2$ desolvation: 400° C., 800 L/hour. Cone: 40 V, N$_2$ cone: 50 L/hour. Analysis mode: MSe continuum, 50-1200 Da, 0.2 s/point. Acquisition of the chromatogram in: Low energy=0 V High energy=20-35 V. LockSpray: Ionization=2.75 kV Acquisition=0.5 s every 15 seconds.

Figure 13:
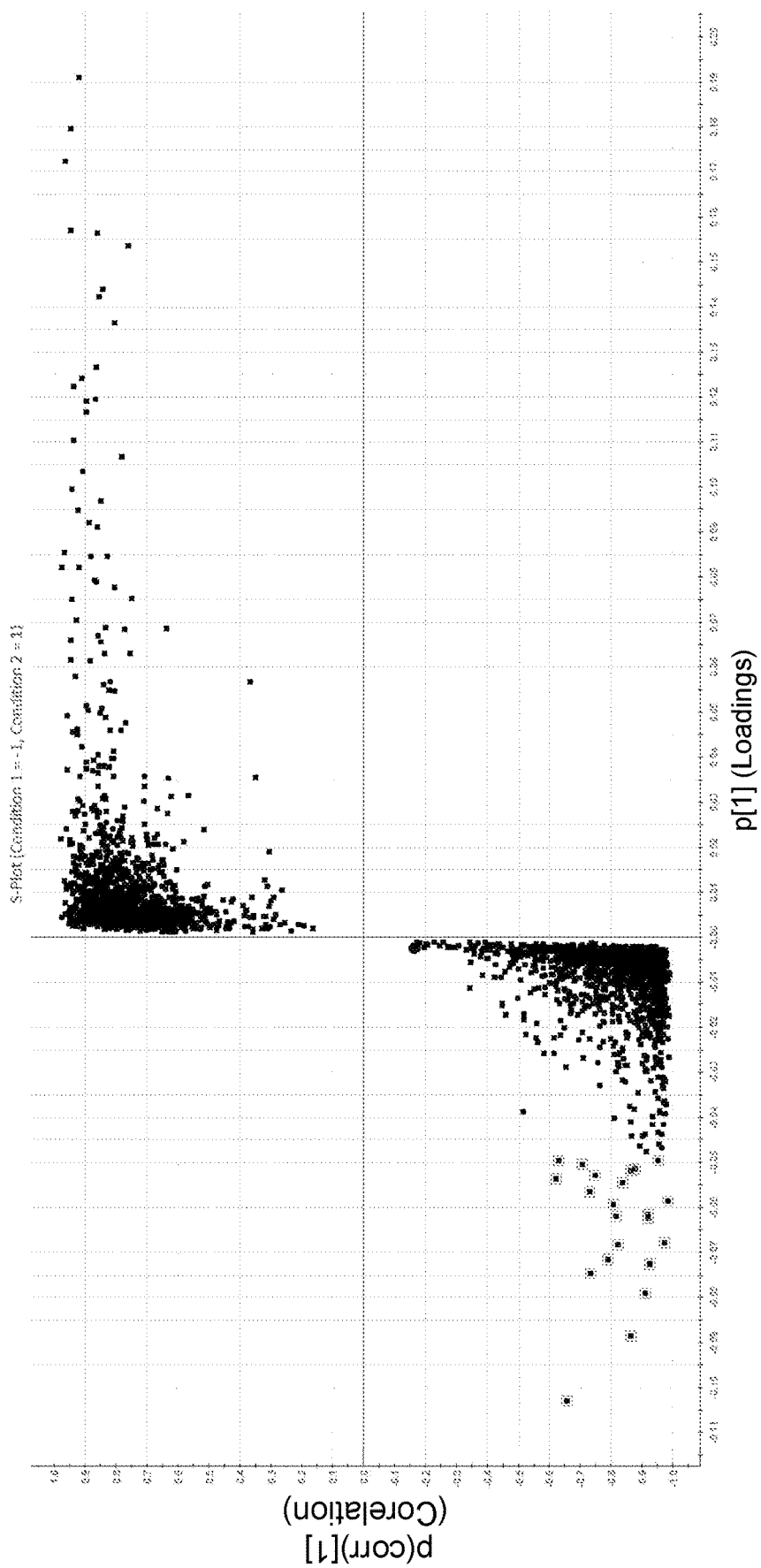
FIG. 13 illustrates a sample "S-plot" that allows the identification of compounds specific to a group of samples.

Identification by Multivariate Statistics of Characteristic Compounds in Off-Flavor Industrial Grade Maple Syrup The results presented here were done using "exact mass" with TOF devices for the determination of the stoichiometric composition of the detected compounds. This is possible by detecting the m/z ratios of the analytes with a precision to the fourth decimal place and by using the observed isotopic ratios for these molecules. These features are useful for non-targeted measurements, which make it possible to highlight compounds specific to a group of samples. In the present example, comparative analyzes were conducted in UPLC-TOF mode MSe for different fractions obtained with good taste maple syrup and off-flavor maple syrup. The measurements obtained for the extracts obtained by the different SPE methods, as described above, were then processed with the Progenesis IQ multivariate statistics software. This software allows, after various operations, to obtain a graph of type "S Plot" as shown on FIG. 13, where each compound is symbolized by a point. In such a representation, the points at the ends of the "S", such as those framed in red in the lower left quadrant of the graph, are those that are specific to one of the two groups of samples that are compared.

This strategy is used to compare regular and off-flavor maple syrup extracts obtained by the SPE methods described above. Table 4 lists the compounds targeted by this methodology for HLB and MCX extractions, as WCX extracts did not reveal any molecules present at significant levels in off-flavor buddy (VR5) syrup samples.

TABLE 4

UPLC-TOF MSe analysis combined with multivariate statistics treatment: retention time, tR, observed in HLB and MCX extracts for compounds targeted as characteristics of off-flavor industrial grade buddy (VR5) syrup samples, with experimental and calculated masses of protonated molecules and their composition elementary

| $t_R$ HLB min. | $t_R$ MCX min. | $[M + H]^+_{exp}$ Da | Elementary Composition | $[M + H]^+_{calc}$ Da |
|---|---|---|---|---|
| | 0.91 | 104.1076 | $C_5H_{14}NO$ | 104.1075 |
| 1.01 | | 136.0622 | $C_5H_6N_5$ | 136.0623 |
| 1.01 | | 268.1042 | $C_{10}H_{14}N_5O_4$ | 268.1046 |
| | 1.10 | 140.0709 | $C_7H_{10}NO_2$ | 140.0712 |
| 1.33 | 1.35 | 110.0605 | $C_6H_8NO$ | 110.0606 |
| 1.51 | 1.53 | 268.1045 | $C_{10}H_{14}N_5O_4$ | 268.1046 |
| | 2.93 | 120.0812 | $C_8H_{10}N$ | 120.0813 |
| 3.16 | | 124.0762 | $C_7H_{10}NO$ | 124.0762 |
| 3.34 | 3.38 | 134.0967 | $C_9H_{12}N$ | 134.0970 |
| 3.60 | | 269.1859 | $C_{14}H_{25}N_2O_3$ | 269.1865 |
| 3.82 | | 269.1861 | $C_{14}H_{25}N_2O_3$ | 269.1865 |
| | 3.99 | 139.0872 | $C_7H_{11}N_2O$ | 139.0871 |
| 4.36 | 4.38 | 144.0815 | $C_{10}H_{10}N$ | 144.0813 |
| 4.36 | | 188.0709 | $C_{11}H_{10}NO_2$ | 188.07712 |
| 4.86 | | 217.1549 | $C_{10}H_{21}N_2O_3$ | 217.1552 |
| 5.01 | 5.03 | 144.0815 | $C_{10}H_{10}N$ | 144.0813 |
| | 6.37 | 193.0497 | $C_{10}H_9O_4$ | 193.0501 |
| | 9.11 | 288.2535 | $C_{16}H_{34}NO_3$ | 288.2539 |
| 11.47 | | 258.1490 | $C_{16}H_{20}NO_2$ | 258.1494 |
| | 12.56 | 319.2250 | $C_{16}H_{27}N_6O$ | 319.2246 |

All the elementary compositions identified, except one, correspond to nitrogen-containing compounds. Amines are known for their rather strong and characteristic smells, which could give off-flavor industrial grade buddy (VR5) maple syrups their unpleasant smell and taste.

EXAMPLE 8

Analysis of Volatile Compounds by GC-MS with "Headspace" Sampling

To detect and identify the volatile compounds present in regular flavor and off-flavor buddy (VR5) maple syrup samples, gas chromatographic analysis coupled with single quadrupole mass spectrometry, GC-MS was performed. The volatile vapor sample is obtained by the "headspace" technique, where 8 grams of maple syrup are placed in a 20 mL flask, which is then heated to 100° C. in the sampler's oven for 30 minutes. A volume of 1 mL is then transferred to the GC/MS inlet. The chromatographic conditions used were as follows:

Inlet temperature/operating mode: 250° C./Split mode 1:1;
Column: Phenomenex ZB-Semivolatiles, 30 m×250 μm×0.25 μm
Carrier gas: He, 35.5 cm/sec, constant flow mode;
Programmation of the oven:

| $T_{Initial}$/Ramp | Rate ° C./min. | Temperature ° C. | Isotherm min. |
|---|---|---|---|
| $T_{Initial}$ | | 50 | 1 |
| Ramp 1 | 3 | 80 | 0 |
| Ramp 2 | 10 | 110 | 0 |
| Ramp 3 | 35 | 240 | 3 |

Figure 14:
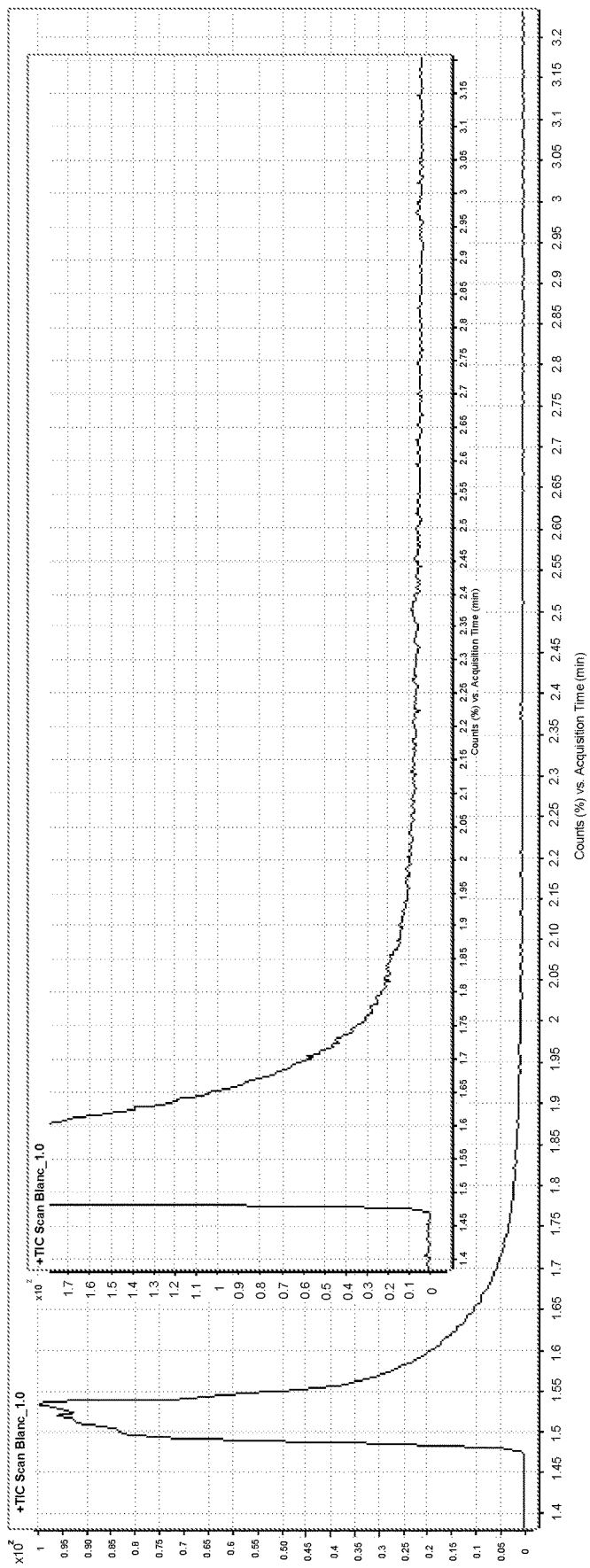
FIG. 14 illustrates a typical blank chromatogram in GC/MS with headspace sampling. An enlargement of the baseline is inserted in a cartridge.

Mass Spectrometer: Source 250° C., Quadrupole 150° C.; Scan mode from 33 to 600 Da, 4.9 cycles/s FIG. 14 shows a typical blank obtained in GC-MS analysis with headspace sampling, using an empty flask. The intense peak between about 1.47 and 1.7 minutes is caused by atmospheric $CO_2$, characterized by a mass/charge ratio, m/z, of 44 Daltons, which is observable throughout the chromatogram. In order to prevent this interference in affecting the identification of the compounds, subtracting the background noise was done for integrating the chromatographic peaks.

Figure 15:
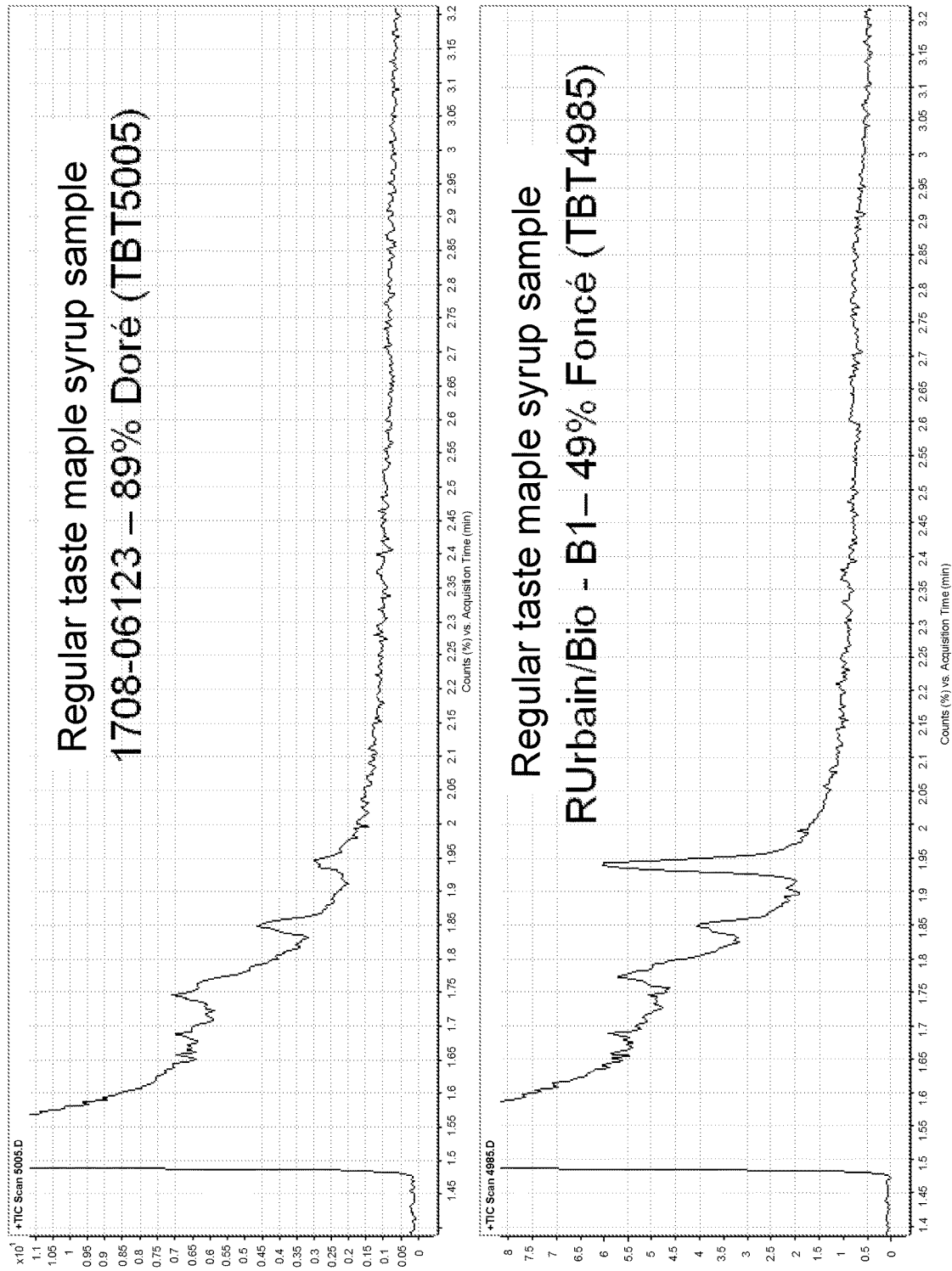
FIG. 15 illustrates chromatograms of good taste maple syrup sample obtained in GC/MS with headspace sampling.

FIG. 15 shows two chromatograms of good taste maple syrup samples, one pale, "1708-06123—89% Golden (TBT5005)", and another dark, "RUrbain/Bio—B1—48% Dark (TBT4985)". In each case, three peaks are observed, in addition to that of $CO_2$, at 1.75, 1.85 and 1.94 minutes. The first does not correspond to any plausible molecules in the spectral data bank. The second would be associated with silanol groups, which could come from a degradation of the chromatographic column by a backbiting reaction, a phenomenon often observed when the stationary phase is brought into contact with water, here steam from the syrup heated to 100° C. The third corresponds to a compound present at different levels in all the tested maple syrup samples with good taste as those of off-flavor industrial quality.

Figure 16:
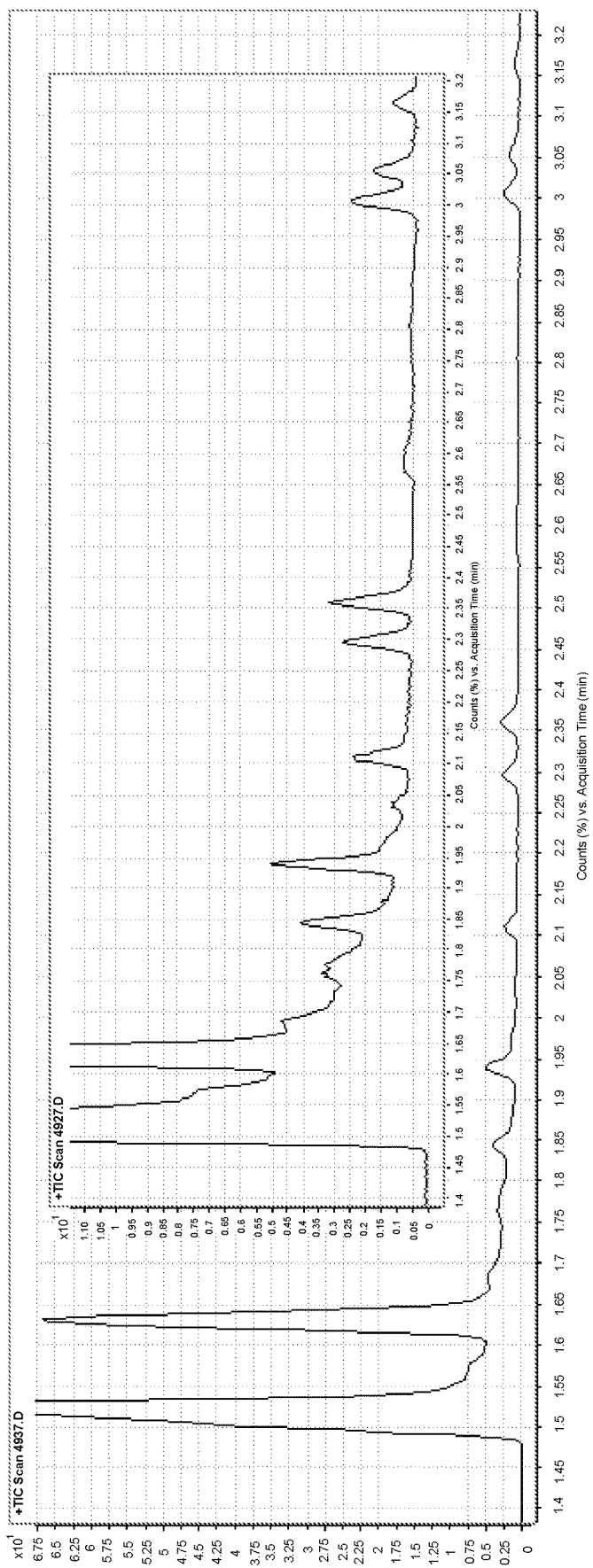
FIG. 16 illustrates a typical chromatogram of off-flavor industrial grade maple syrup buddy VR5, obtained in GC/MS with headspace sampling for sample "1105.8-21% Very Dark (TBT4937)".

FIG. 16 shows a typical chromatogram of the majority of off-flavor industrial grade syrups buddy (VR5) obtained for syrup "1105.8-21% Very Dark (TBT4937)". In addition to the observable peak at 1.94 min. which is also present in good taste maple syrups, there are 9 peaks which correspond to identifiable products identified in the mass spectra bank, having the retention times of 1.63/1.84/2.04/2.11/2.30/2.36/3.00/3.06 and 3.17 minutes. No significant peak was observed at longer times for all samples analyzed.

The following tables 6 to 25 compile the compounds identified by "headspace" GC/MS for the different syrups having good taste and off-flavor buddy (VR5). Each table list:

the retention time, tR;
The potentially identified compound (s);
The scores obtained on 1000 in "Fit" and "Retro-Fit", R-Fit;
the probability of correct identification;
The positions, 1st, 2nd, 3rd, . . . where the identified compounds are found.

The identifications were obtained by comparison with the National Institute of Standards and Technology (NIST) GC-MS mass spectrophotometric library. The Fit scores indicate the quality of the comparison of the experimental mass spectrum with the library spectrum, whereas the R-Fit assesses the adequacy between the m/z ratios and their intensities in the reference spectrum with respect to the experimental spectrum. Also, since the library often contains several reference spectra for a compound, which have only minor differences between them, a compound can be identified with respect to several of the spectra in the library.

According to the chromatograms shown in FIG. 16, the off-flavor industrial grade maple syrup samples buddy (VR5) generally have 9 or 10 peaks, depending on the presence of a compound identified by the NIST library as "ethyl acetate", at a time retention time of 2.04 minutes. Among these syrups, the "1103.8-55% Amber (TBT4934)" is an exception, in Table 9, where there are some of the same compounds found in the other off-flavor samples, but where the peaks at 2.04/2.11/3.01 and 3.06 minutes are absent.

Of the compounds detected, the peak at 1.63 minutes, is identified as ethanol (Tables 6 to 19), with confidence percentages of 78 to 97% and values of "Fit" and "R-Fit" above 950/1000 in almost all cases. Since the maple syrups were transferred to "Mason" jars for easier sampling, the possibility of fermentation during refrigeration appeared to be a probable reason for the presence of this compound.

TABLE 5

List of maple syrup samples tested

| Code | Class of syrup | Quantity | Light Transmission/Grade | No. TBT |
|---|---|---|---|---|
| — | Buddy | 1 × 25.3 kg | Amber | 4872 |
| — | Buddy | Sac | Very dark | 4873 |
| 303.7 | Buddy | 3 × 540 mL | 48%/Dark | 4928, 4929, 4930 |
| 304.6 | Buddy | 3 × 540 mL | 57%/Amber | 4931, 4932, 4933 |
| 1103.8 | Buddy | 3 × 540 mL | 55%/Amber | 4934, 4935, 4936 |
| 1105.8 | Buddy | 2 × 540 mL | 21%/Very Dark | 4937, 4938 |
| 1105.24 | Buddy | 1 × 540 mL | 21%/Very Dark | 4939 |
| 1106.6 | Buddy | 3 × 540 mL | 45%/Dark | 4940, 4941, 4942 |
| 1107.5 | Buddy | 3 × 540 mL | 54%/Amber | 4943, 4944, 4948 |
| 1107.21 | Buddy | 1 × 540 mL | 54%/Amber | 4945 |
| 1113.7 | Buddy | 2 × 540 mL | 50%/Dark | 4946, 4947 |
| 1118.6 | Buddy | 3 × 540 mL | 51%/Amber | 4949, 4950, 4951 |
| 1713 07033 DO | Good taste/regular syrup | 3 × 540 mL | 83%/Golden | 4952, 4953, 4954 |
| 1713 07145 RO | Good taste/regular syrup | 3 × 540 mL | 19%/Very Dark | 4955, 4956, 4957 |
| RUrbain/Bio-C1 | No2-sappy (VR1) | 4 × 540 mL | 33%/Very Dark | 4989, 4990, 4991, 4992 |
| RUrbain/Bio-A1 | No1 - regular syrup EXTRA-CLAIR | 4 × 540 mL | 77%/Golden | 4981, 4982, 4983, 4984 |
| RUrbain/Bio-B1 | No1 - regular syrup | 4 × 540 mL | 48%/Dark | 4985, 4986, 4987, 4988 |
| SF1 | Good taste/regular syrup | 4 × 540 mL | Golden | 4993, 4994, 4995, 4996 |
| SF2 | Good taste/regular syrup | 4 × 540 mL | Amber | 4997, 4998, 4999, 5000 |
| SF3 | Good taste/regular syrup | 4 × 540 mL | Dark | 5001, 5002, 5003, 5004 |
| 1708-06123 | Good taste/regular syrup | 3 × 540 ml | 89%/Golden | 5005 |
| 1708-06797 | Good taste/regular syrup | 3 × 540 ml | 87%/Golden | 5006 |
| 1716-00026 | Good taste/regular syrup | 3 × 540 ml | 84%/Golden | 5007 |
| 1716-00128 | Good taste/regular syrup | 3 × 540 ml | 88%/Golden | 5008 |
| 1704-09320 | Good taste/regular syrup | 3 × 540 ml | 10%/Very Dark | 5009 |
| 1705-02212 | Good taste/regular syrup | 3 × 540 ml | 23%/Very Dark | 5010 |
| 1704-09383 | Good taste/regular syrup | 3 × 540 ml | 20%/Very Dark | 5011 |
| 1705-02347 | Good taste/regular syrup | 3 × 540 ml | 12%/Very Dark | 5012 |
| 1708-06849 | Buddy | 3 × 540 ml | 83%/Golden | 5013 |

TABLE 6

Identification of compounds in syrup Code 303.7 - VR5 - 48% Dark (TBT4928) by headspace-GC-MS.

| $t_R$ (min.) | Compound | Fit | R-Fit | %$_{Confidence}$ | Positions |
|---|---|---|---|---|---|
| 1.63 | Ethanol | 969 | 974 | 80 | 1-3 |
| 1.84 | 2-Methyl-propanal | 614 | 848 | 42 | 1-4 |
| 1.94 | Acetic acid ethenyl ester | 894 | 924 | 72 | 1, 4, 6 |
|  | 2,3-Butanedione | 869 | 908 | 22 | 2, 3, 5 |
| 2.11 | 2-Methyl-propan-1-ol | 661 | 916 | 58 | 1-4 |
| 2.30 | 3-Methyl-butanal | 810 | 876 | 73 | 1-3, 5 |
|  | Pentanal | 787 | 835 | 15 | 4, 6 |
| 2.36 | 2-Methyl-butanal | 829 | 902 | 84 | 1-3 |
| 3.01 | 3-Methyl-butan-1-ol | 737 | 866 | 30 | 1-3 |
| 3.06 | 2-Methyl-butan-1-ol | 545 | 814 | 25 | 1-5 |
| 3.17 | Dimethyldisulfure (DMDS) | 805 | 864 | 93 | 1-5 |

TABLE 7

Identification of compounds in syrup Code 304.6 - VR5 - 57% Amber (TBT4931) by headspace-GC-MS.

| $t_R$ (min.) | Compound | Fit | R-Fit | %$_{Confidence}$ | Positions |
|---|---|---|---|---|---|
| 1.63 | Ethanol | 950 | 958 | 78 | 1-3 |
| 1.84 | 2-Methyl-propanal | 603 | 869 | 59 | 1, 2, 5, 6 |
| 1.94 | Acetic acid ethenyl ester | 856 | 932 | 76 | 1, 4, 5 |
|  | 2,3-Butanedione | 822 | 905 | 19 | 2, 3 |
| 2.04 | Ethylacetate | 849 | 924 | 93 | 1-4 |
| 2.11 | 2-Methyl-propan-1-ol | 675 | 910 | 63 | 1-4 |
| 2.30 | 3-Methyl-butanal | 850 | 899 | 80 | 1-3, 5 |
|  | Pentanal | 780 | 845 | 12 | 4, 6 |
| 2.36 | 2-Methyl-butanal | 827 | 883 | 76 | 1-3 |
| 3.01 | 3-Methyl-butan-1-ol | 765 | 848 | 15 | 1-3, 6 |
| 3.06 | 2-Methyl-butan-1-ol | 576 | 802 | 28 | 1-6 |
| 3.17 | Dimethyldisulfide (DMDS) | 853 | 872 | 91 | 1-5 |

TABLE 8

Identification of compounds in syrup Code 304.6 - VR5 - 57% Amber (TBT4932, same lot as TBT4931, box opened just before the analysis) by headspace-GC-MS.

| $t_R$ (min.) | Compound | Fit | R-Fit | %$_{Confidence}$ | Positions |
|---|---|---|---|---|---|
| 1.63 | Ethanol | 955 | 964 | 81 | 1-3 |
| 1.84 | 2-Methyl-propanal | 560 | 803 | 13 | 1, 2, 4 |
| 1.94 | Acetic acid ethenyl ester | 849 | 919 | 77 | 1, 3, 5 |
|  | 2,3-Butanedione | 806 | 878 | 17 | 2, 4, 6 |
| 2.03 | Ethylacetate | 821 | 896 | 92 | 1-4 |
| 2.11 | 2-Methyl-propan-1-ol | 715 | 888 | 64 | 1-4 |
| 2.29 | 3-Methyl-butanal | 811 | 862 | 74 | 1-3, 5 |
|  | Pentanal | 810 | 860 | 16 | 4, 6 |
| 2.36 | 2-Methyl-butanal | 794 | 849 | 63 | 1-3 |
| 3.02 | 3-Methyl-butan-1-ol | 813 | 893 | 46 | 1, 2 |
| 3.06 | 2-Methyl-butan-1-ol | 645 | 804 | 28 | 1-5 |
| 3.17 | Dimethyldisulfide (DMDS) | 907 | 923 | 97 | 1-5 |

TABLE 9

Identification of compounds in syrup Code 1103.8 - VR5 - 55% Amber (TBT4934) by headspace-GC-MS.

| $t_R$ (min.) | Compound | Fit | R-Fit | %$_{Confidence}$ | Positions |
|---|---|---|---|---|---|
| 1.63 | Ethanol | 927 | 934 | 80 | 1-3 |
| 1.84 | 2-Methyl-propanal | 593 | 825 | 33 | 1-3 |
| 1.94 | Acetic acid ethenyl ester | 868 | 928 | 80 | 1, 4, 6 |
|  | 2,3-Butanedione | 817 | 886 | 16 | 2, 3, 5 |
| 2.30 | 3-Methyl-butanal | 822 | 868 | 76 | 1-3, 5 |
|  | Pentanal | 779 | 822 | 16 | 4, 6 |
| 2.36 | 2-Methyl-butanal | 821 | 884 | 69 | 1-3 |
| 3.17 | Dimethyldisulfide (DMDS) | 837 | 869 | 91 | 1-5 |

TABLE 10

Identification of compounds in syrup Code 1105.8 - VR5 - 21% Very dark (TBT4937) by headspace-GC-MS.

| $t_R$ (min.) | Compound | Fit | R-Fit | %$_{Confidence}$ | Positions |
|---|---|---|---|---|---|
| 1.63 | Ethanol | 938 | 941 | 84 | 1-3 |
| 1.84 | 2-Methyl-propanal | 692 | 840 | 67 | 1-4 |
| 1.94 | Acetic acid ethenyl ester | 801 | 902 | 53 | 1, 5 |
|  | 2,3-Butanedione | 788 | 892 | 34 | 2, 3, 4 |
| 2.04 | Ethylacetate | 527 | 762 | 19 | 1-3 |
| 2.11 | 2-Methyl-propan-1-ol | 766 | 845 | 75 | 1-4 |
| 2.30 | 3-Methyl-butanal | 814 | 903 | 82 | 1-4 |
|  | Pentanal | 733 | 840 | 9 | 5, 6 |
| 2.36 | 2-Methyl-butanal | 842 | 883 | 78 | 1-3 |
| 3.00 | 3-Methyl-butan-1-ol | 873 | 892 | 47 | 1-4 |
| 3.06 | 2-Methyl-butan-1-ol | 675 | 790 | 13 | 1, 3 |
| 3,.17 | Dimethyldisulfide (DMDS) | 762 | 847 | 86 | 1-5 |

TABLE 11

Identification of compounds in the syrup Code 1105.8 - VR5 - 21% Very dark (TBT4938, same batch as TBT4937, box opened just before the analysis) by headspace-GC-MS.

| $t_R$ (min.) | Compound | Fit | R-Fit | %$_{Confidence}$ | Positions |
|---|---|---|---|---|---|
| 1.63 | Ethanol | 960 | 969 | 89 | 1-3 |
| 1.84 | 2-Methyl-propanal | 659 | 846 | 47 | 1-4 |
| 1.94 | Acetic acid ethenyl ester | 901 | 925 | 85 | 1, 5 |
|  | 2,3-Butanedione | 831 | 864 | 12 | 2-4, 6 |
| 2.04 | Ethylacetate | 541 | 793 | 23 | 1, 2, 4 |
| 2.11 | 2-Methyl-propan-1-ol | 787 | 838 | 73 | 1-4 |
| 2.30 | 3-Methyl-butanal | 861 | 887 | 78 | 1-4 |
|  | Pentanal | 800 | 851 | 14 | 5, 6 |
| 2.36 | 2-Methyl-butanal | 869 | 906 | 80 | 1-3 |
| 3.00 | 3-Methyl-butan-1-ol | 872 | 895 | 48 | 1-3 |
| 3.06 | 2-Methyl-butan-1-ol | 737 | 805 | 35 | 1-4, 6 |
| 3,.7 | Dimethyldisulfide (DMDS) | 812 | 846 | 90 | 1-5 |

TABLE 12

Identification of compounds in syrup Code 1105.24 - VR5 - 21% Very dark (TBT4939, 1st replica) by headspace-GC-MS.

| $t_R$ (min.) | Compound | Fit | R-Fit | %$_{Confidence}$ | Positions |
|---|---|---|---|---|---|
| 1.63 | Ethanol | 956 | 961 | 97 | 1-3 |
| 1.84 | 2-Methyl-propanal | 584 | 812 | 28 | 1-4 |
| 1.94 | Acetic acid ethenyl ester | 867 | 923 | 64 | 1, 5, 6 |
|  | 2,3-Butanedione | 848 | 887 | 31 | 2, 3, 4 |
| 2.11 | 2-Methyl-propan-1-ol | 785 | 918 | 91 | 1-4 |
| 2.29 | 3-Methyl-butanal | 801 | 869 | 74 | 1-4 |
|  | Pentanal | 729 | 823 | 12 | 5, 6 |
| 2.36 | 2-Methyl-butanal | 784 | 865 | 60 | 1-3 |
| 3.01 | 3-Methyl-butan-1-ol | 841 | 909 | 62 | 1-4 |
| 3.05 | 2-Methyl-butan-1-ol | 655 | 813 | 31 | 1-6 |
| 3.17 | Dimethyldisulfide (DMDS) | 702 | 821 | 79 | 1-5 |

TABLE 13

Identification of compounds in syrup Code 1105.24 - VR5 - 21% Very dark (TBT4939, 2nd replica) by headspace-GC-MS.

| $t_R$ (min.) | Compound | Fit | R-Fit | %$_{Confidence}$ | Positions |
|---|---|---|---|---|---|
| 1.64 | Ethanol | 955 | 962 | 82 | 1-3 |
| 1.85 | 2-Methyl-propanal | 635 | 838 | 43 | 1-3 |
| 1.94 | Acetic acid ethenyl ester | 912 | 929 | 80 | 1, 3, 4 |
|  | 2,3-Butanedione | 852 | 892 | 16 | 2, 5, 6 |
| 2.11 | 2-Methyl-propan-1-ol | 787 | 844 | 74 | 1-4 |
| 2.30 | 3-Methyl-butanal | 844 | 886 | 74 | 1-4 |
|  | Pentanal | 792 | 843 | 15 | 5, 6 |
| 2.36 | 2-Methyl-butanal | 854 | 897 | 85 | 1-3 |
| 3.02 | 3-Methyl-butan-1-ol | 844 | 885 | 37 | 1-2 |
| 3.05 | 2-Methyl-butan-1-ol | 727 | 798 | 49 | 1-5 |
| 3.17 | Dimethyldisulfide (DMDS) | 785 | 871 | 90 | 1-5 |

TABLE 14

Identification of compounds in syrup Code 1105.24 - VR5 - 21% Very dark (TBT4939, 3rd replica) by headspace-GC-MS.

| $t_R$ (min.) | Compound | Fit | R-Fit | %$_{Confidence}$ | Positions |
|---|---|---|---|---|---|
| 1.64 | Ethanol | 960 | 968 | 81 | 1-3 |
| 1.85 | 2-Methyl-propanal | 514 | 787 | 7 | 1, 4 |
| 1.94 | Acetic acid ethenyl ester | 884 | 934 | 80 | 1, 5, 6 |
|  | 2,3-Butanedione | 833 | 891 | 16 | 2, 3, 4 |

TABLE 14-continued

Identification of compounds in syrup Code 1105.24 - VR5 - 21% Very dark (TBT4939, 3rd replica) by headspace-GC-MS.

| $t_R$ (min.) | Compound | Fit | R-Fit | %$_{Confidence}$ | Positions |
|---|---|---|---|---|---|
| 2.03 | Ethylacetate | 538 | 820 | 19 | 1-4 |
| 2.11 | 2-Methyl-propan-1-ol | 778 | 870 | 65 | 1-4 |
| 2.18 | Acetic acid | 921 | 934 | 81 | 1, 5 |
| 2.30 | 3-Methyl-butanal | 834 | 895 | 76 | 1-3, 6 |
|  | Pentanal | 778 | 848 | 14 | 2, 4 |
| 2.36 | 2-Methyl-butanal | 854 | 902 | 82 | 1-3 |
| 3.02 | 3-Methyl-butan-1-ol | 856 | 885 | 30 | 1-2, 4 |
| 3.05 | 2-Methyl-butan-1-ol | 741 | 818 | 34 | 1-6 |
| 3.17 | Dimethyldisulfide (DMDS) | 800 | 866 | 90 | 1-5 |

TABLE 15

Identification of compounds in syrup Code 1106.6 - VR5 - 45% Dark (TBT4940) by headspace-GC-MS.

| $t_R$ (min.) | Compound | Fit | R-Fit | %$_{Confidence}$ | Positions |
|---|---|---|---|---|---|
| 1.64 | Ethanol | 967 | 975 | 82 | 1-3 |
| 1.85 | 2-Methyl-propanal | 606 | 856 | 43 | 1-2 |
| 1.94 | Acetic acid ethenyl ester | 888 | 920 | 85 | 1, 3, 4 |
|  | 2,3-Butanedione | 812 | 829 | 11 | 2, 5, 6 |
| 2.04 | Ethylacetate | 808 | 871 | 89 | 1-4 |
| 2.11 | 2-Methyl-propan-1-ol | 758 | 820 | 78 | 1-4 |
| 2.30 | 3-Methyl-butanal | 851 | 895 | 74 | 1-3 |
|  | Pentanal | 802 | 867 | 15 | 4, 6 |
| 2.36 | 2-Methyl-butanal | 803 | 889 | 79 | 1-3 |
| 3.02 | 3-Methyl-butan-1-ol | 869 | 897 | 50 | 1, 2, 4 |
| 3.05 | 2-Methyl-butan-1-ol | 735 | 825 | 51 | 1, 2, 4-6 |
| 3.17 | Dimethyldisulfide (DMDS) | 827 | 868 | 91 | 1-5 |

TABLE 16

Identification of compounds in syrup Code 1107.5 - VR5 - 54% Amber (TBT4943) by headspace-GC-MS.

| $t_R$ (min.) | Compound | Fit | R-Fit | %$_{Confidence}$ | Positions |
|---|---|---|---|---|---|
| 1.64 | Ethanol | 955 | 964 | 79 | 1-3 |
| 1.85 | 2-Methyl-propanal | 604 | 851 | 40 | 1-3 |
| 1.94 | Acetic acid ethenyl ester | 848 | 911 | 76 | 1, 3, 6 |
|  | 2,3-Butanedione | 813 | 852 | 19 | 2, 4, 5 |
| 2.04 | Ethylacetate | 568 | 795 | 32 | 1, 3, 5, 6 |
| 2.11 | 2-Methyl-propan-1-ol | 759 | 853 | 76 | 1-4 |
| 2.30 | 3-Methyl-butanal | 810 | 867 | 76 | 1-4 |
|  | Pentanal | 749 | 825 | 13 | 5, 6 |
| 2.36 | 2-Methyl-butanal | 841 | 875 | 67 | 1-3 |
| 3.02 | 3-Methyl-butan-1-ol | 859 | 884 | 52 | 1, 2, 4 |
| 3.05 | 2-Methyl-butan-1-ol | 708 | 816 | 40 | 1-5 |
| 3.17 | Dimethyldisulfide (DMDS) | 838 | 887 | 91 | 1-5 |

TABLE 17

Identification of compounds in syrup Code 1107.21 - VR5 - 54% Amber (TBT4945) by headspace-GC-MS.

| $t_R$ (min.) | Compound | Fit | R-Fit | %$_{Confidence}$ | Positions |
|---|---|---|---|---|---|
| 1.64 | Ethanol | 958 | 966 | 88 | 1-3 |
| 1.85 | 2-Methyl-propanal | 566 | 838 | 24 | 1, 3-5 |
| 1.94 | Acetic acid ethenyl ester | 819 | 910 | 78 | 1, 5, 6 |
|  | 2,3-Butanedione | 767 | 859 | 16 | 2-4 |

TABLE 17-continued

Identification of compounds in syrup Code 1107.21 - VR5 - 54% Amber (TBT4945) by headspace-GC-MS.

| $t_R$ (min.) | Compound | Fit | R-Fit | %$_{Confidence}$ | Positions |
|---|---|---|---|---|---|
| 2.11 | 2-Methyl-propan-1-ol | 727 | 809 | 53 | 1-4 |
| 2.30 | 3-Methyl-butanal | 807 | 863 | 78 | 1-4 |
|  | Pentanal | 772 | 828 | 12 | 5, 6 |
| 2.36 | 2-Methyl-butanal | 790 | 851 | 69 | 1-3 |
| 3.02 | 3-Methyl-butan-1-ol | 835 | 873 | 32 | 1, 2, 4, 6 |
| 3.05 | 2-Methyl-butan-1-ol | 704 | 792 | 40 | 1-6 |
| 3.17 | Dimethyldisulfide (DMDS) | 819 | 862 | 92 | 1-5 |

TABLE 18

Identification of compounds in syrup Code 1113.7 - VR5 - 50% Amber (TBT4946) by headspace-GC-MS.

| $t_R$ (min.) | Compound | Fit | R-Fit | %$_{Confidence}$ | Positions |
|---|---|---|---|---|---|
| 1.64 | Ethanol | 959 | 967 | 89 | 1-3 |
| 1.85 | 2-Methyl-propanal | 584 | 860 | 21 | 1-3 |
| 1.94 | Acetic acid ethenyl ester | 837 | 898 | 80 | 1, 5, 6 |
|  | 2,3-Butanedione | 780 | 821 | 15 | 2-4 |
| 2.04 | Ethylacetate | 800 | 888 | 85 | 1-4 |
| 2.11 | 2-Methyl-propan-1-ol | 760 | 890 | 74 | 1-4 |
| 2.30 | 3-Methyl-butanal | 829 | 875 | 73 | 1-4 |
|  | Pentanal | 776 | 847 | 14 | 5, 6 |
| 2.36 | 2-Methyl-butanal | 809 | 878 | 57 | 1-3 |
| 3.02 | 3-Methyl-butan-1-ol | 801 | 856 | 26 | 1, 2, 5 |
| 3.05 | 2-Methyl-butan-1-ol | 580 | 747 | 11 | 1, 3, 4 |
| 3.17 | Dimethyldisulfide (DMDS) | 797 | 834 | 93 | 1-5 |

TABLE 19

Identification of compounds in syrup Code 1118.6 - VR5 - 51% Amber (TBT4949) by headspace-GC-MS.

| $t_R$ (min.) | Compound | Fit | R-Fit | %$_{Confidence}$ | Positions |
|---|---|---|---|---|---|
| 1.64 | Ethanol | 959 | 967 | 89 | 1-3 |
| 1.85 | 2-Methyl-propanal | 629 | 862 | 44 | 1, 2, 4 |
| 1.94 | Acetic acid ethenyl ester | 865 | 915 | 79 | 1, 4, 6 |
|  | 2,3-Butanedione | 819 | 856 | 17 | 2, 3, 5 |
| 2.04 | Ethylacetate | 636 | 852 | 66 | 1-4 |
| 2.11 | 2-Methyl-propan-1-ol | 796 | 884 | 77 | 1-4 |
| 2.30 | 3-Methyl-butanal | 827 | 881 | 75 | 1-4 |
|  | Pentanal | 754 | 831 | 10 | 5, 6 |
| 2.36 | 2-Methyl-butanal | 816 | 872 | 71 | 1-3 |
| 3.02 | 3-Methyl-butan-1-ol | 873 | 902 | 47 | 1-3 |
| 3.05 | 2-Methyl-butan-1-ol | 717 | 783 | 50 | 1-6 |
| 3.17 | Dimethyldisulfide (DMDS) | 841 | 863 | 91 | 1-5 |

TABLE 20

Identification of compounds in syrup Code RURbain/Bio-C1 - No 2-Fin sap (VR1) - 33% Very dark (TBT4989, 1st replica) by headspace-GC-MS.

| $t_R$ (min.) | Compound | Fit | R-Fit | %$_{Confidence}$ | Positions |
|---|---|---|---|---|---|
| 1.94 | Acetic acid ethenyl ester | 891 | 917 | 82 | 1, 5, 6 |
|  | 2,3-Butanedione | 830 | 843 | 14 | 2-4 |
| 1.99 | 3-Methyl-furane | 653 | 858 | 46 | 1, 5 |
|  | 2-Methyl-furane | 636 | 837 | 25 | 2-4, 6 |
| 2.11 | Acetic Acid | 744 | 905 | 80 | 1-3, 5, 6 |

TABLE 20-continued

Identification of compounds in syrup Code RURbain/Bio-C1 - No 2-Fin sap (VR1) - 33% Very dark (TBT4989, 1st replica) by headspace-GC-MS.

| $t_R$ (min.) | Compound | Fit | R-Fit | %$_{Confidence}$ | Positions |
|---|---|---|---|---|---|
| 2.36 | 2-Methyl-butanal | 597 | 830 | 32 | 1, 2, 4 |
| 2.56 | 1-Hydroxy-propan-2-one | 750 | 822 | 67 | 1-3 |
| | Methyl ester of acetic acid | 677 | 764 | 9 | 4,5 |

TABLE 21

Identification of compounds in syrup Code RUrbain/Bio-C1 - No 2-Fine sap (VR1) - 33% Very dark (TBT4989, 2nd replica) by headspace-GC-MS.

| $t_R$ (min.) | Compound | Fit | R-Fit | %$_{Confidence}$ | Positions |
|---|---|---|---|---|---|
| 1.94 | Acetic acid ethenyl ester | 917 | 938 | 81 | 1, 4, 5 |
| | 2,3-Butanedione | 867 | 898 | 16 | 2, 3, 6 |
| 1.99 | 3-Methyl-furane | 624 | 878 | 31 | 1, 4-6 |
| | 2-Methyl-furane | 611 | 780 | 20 | 2, 3 |
| 2.13 | Acetic acid | 892 | 916 | 80 | 1-4, 6 |
| 2.36 | 2-Methyl-butanal | 614 | 837 | 38 | 1-3 |
| 2.58 | 1-Hydroxy-propan-2-one | 833 | 869 | 69 | 1, 2 |
| | Methyl ester of acetic acid | 782 | 838 | 14 | 3, 5, 6 |

TABLE 20

Identification de Compounds dans le sirop Code SF2 - Sirop régulier - Ambré (TBT4997) par headspace-GC/MS.

| $t_R$ (min.) | Compound | Fit | R-Fit | %$_{Confidence}$ | Positions |
|---|---|---|---|---|---|
| 1.94 | Acetic acid ethenyl ester | 886 | 925 | 88 | 1, 2 |
| | 2,3-Butanedione | 800 | 835 | 8 | 3-5 |

TABLE 22

Identification of compounds in syrup Code RUrbain/Bio-B1 - No. 1-Regular Syrup - 48% Dark (TBT4985) by headspace-GC-MS.

| $t_R$ (min.) | Compound | Fit | R-Fit | %$_{Confidence}$ | Positions |
|---|---|---|---|---|---|
| 1.94 | Acetic acid ethenyl ester | 912 | 935 | 80 | 1, 5, 6 |
| | 2,3-Butanedione | 866 | 899 | 17 | 2-4 |

TABLE 23

Identification of compounds in syrup Code 1708-06123 - Tasty/regular syrup - 89% Golden (TBT5005) by headspace-GC-MS.

| $t_R$ (min.) | Compound | Fit | R-Fit | %$_{Confidence}$ | Positions |
|---|---|---|---|---|---|
| 1.94 | 2,3-Butanedione | 566 | 895 | 21 | 1, 3, 5 |
| | Acetic acid ethenyl ester | 549 | 913 | 11 | 2 |

TABLE 24

Identification of compounds in syrup Code 1705-02212 - Tasty/regular syrup - 23% Very dark (TBT5010) by headspace-GC-MS.

| $t_R$ (min.) | Compound | Fit | R-Fit | %$_{Confidence}$ | Positions |
|---|---|---|---|---|---|
| 1.94 | Acetic acid ethenyl ester | 915 | 928 | 80 | 1, 4, 6 |
| | 2,3-Butanedione | 867 | 891 | 17 | 2, 3, 5 |

TABLE 25

Identification of compounds in syrup Code 1708-06849 - VR5 - 83% Golden (TBT5013) by headspace-GC-MS.

| $t_R$ (min.) | Compound | Fit | R-Fit | %$_{Confidence}$ | Positions |
|---|---|---|---|---|---|
| 1.94 | Acetic acid ethenyl ester | 799 | 912 | 77 | 1, 2, 5 |
| | 2,3-Butanedione | 746 | 835 | 12 | 3, 4, 6 |
| 2.30 | 3-Methyl-butanal | 753 | 851 | 68 | 1-4 |
| 2.36 | 2-Methyl-butanal | 698 | 849 | 42 | 1-3 |
| 3.17 | Dimethyldisulfide (DMDS) | 827 | 863 | 93 | 1-5 |

Other compounds identified by headspace sampling GC/MS include three aldehydes, two esters, three alcohols and dimethyldisulfide (DMDS). Moreover, it should be noted that aldehydes and DMDS are odorous compounds, quite likely to confer an unpleasant odor to off-flavor maple syrups (VR5).

Figure 17:
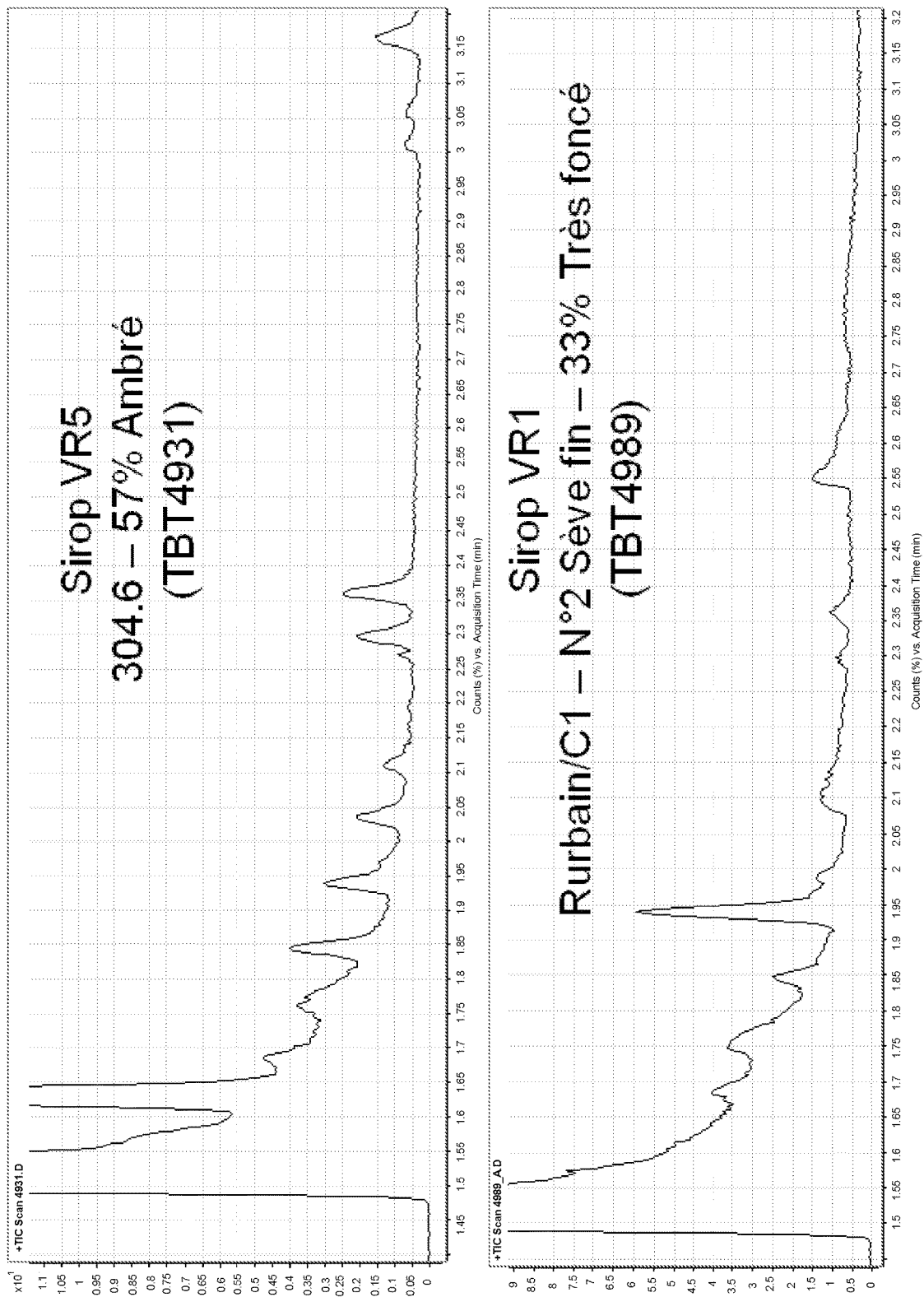
FIG. 17 illustrates a comparison of a chromatogram typical of the majority of buddy (VR5) maple syrup analyzed with a chromatogram of syrup with sap defect (VR1) RUrbain/Bio-C1—N° 2 Fine sap—33% Very dark, obtained in GC-MS with headspace sampling.

However, it is also important to compare the compounds identified for syrup with sap defect "RUrbain/Bio-C1—N ° 2-Fine Sap (VR1)—33% Very Dark (TBT4989)" sap syrup, in Tables 20 and 21, to the other "VR5" of Tables 6 to 19. Except for the peak at 1.94 minutes, present in all analyzed samples including good taste maples syrups (Tables 22 to 25), the compounds identified for this sample differ from those for off-flavor buddy (VR5) except for 2-methyl-butanal. FIG. 17 illustrates how well this syrup with sap defect stands out from the off-flavor industrial grade buddy (VR5) maple syrups. GC-MS analysis with headspace sampling confirm that there are different maple syrup defects that cause downgrading to syrup with sap defect or buddy (VR5).

EXAMPLE 9

Semi-Quantitative Analysis of Ethanol and DMDS by GC-MS with Headspace Sampling

Figure 18:
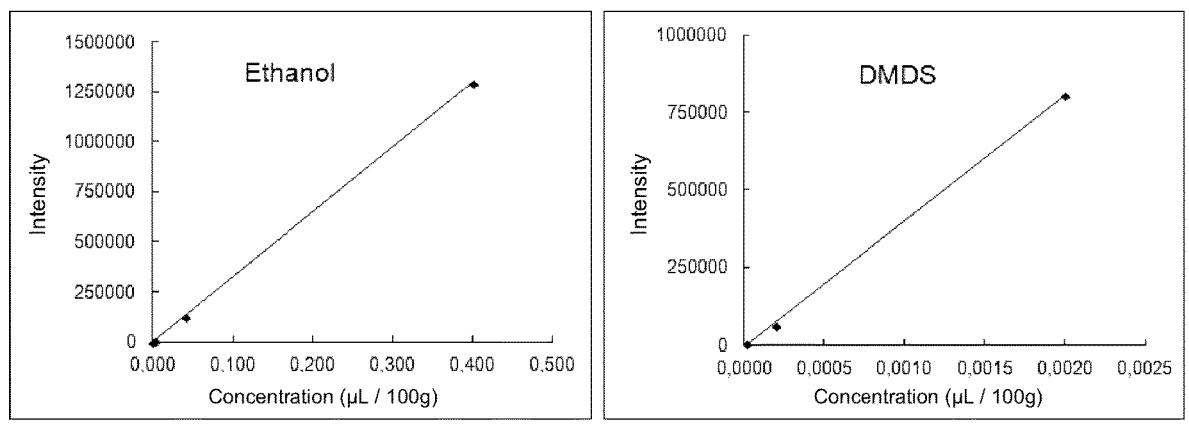
FIG. 18 illustrates a calibration curve used for semi-quantitative analysis of ethanol and DMDS in off-flavor buddy (VR5) maple syrups samples. Concentration is presented as µL/100 g.

Semi-quantitative analysis was conducted to determine the approximate levels of ethanol and dimethyldisulfide in off-flavor VR5 maple syrup samples. The two-point calibration curves, in addition to a blank, are shown in FIG. 18 and the results are shown in Table 26.

TABLE 26

Approximate amounts of ethanol and DMDS in decommissioned buddy maple syrups (VR5) and syrup with sap defect (VR1), as well as in regular syrup.

| Identification | Ethanol concentration µL/100 g | DMDS concentration µL/100 g |
|---|---|---|
| 303.7 - VR5 - 48% Dark | 5.0 | 0.0021 |
| 304.6 - VR5 - 57% Amber | 4.8 | 0.0031 |
| 1103.8 - VR5 - 55% Amber | 3.3 | 0.0030 |

TABLE 26-continued

Approximate amounts of ethanol and DMDS in decommissioned buddy maple syrups (VR5) and syrup with sap defect (VR1), as well as in regular syrup.

| Identification | Ethanol concentration µL/100 g | DMDS concentration µL/100 g |
|---|---|---|
| 1105.8 - VR5 - 21% Very dark | 17 | 0.0022 |
| 1107.5 - VR5 - 54% Amber | 8.3 | 0.0022 |
| 1708-06849 - VR5 - 83% Golden | <LD | 0.0038 |
| RUrbain/Bio-C1 - No2- Sappy VR1 - 33% Very dark | <LD | <LD |
| 1708-06123 - Good taste- 89% Golden | <LD | <LD |

The results from table 26 above suggest that there are different chemical compositions for decommissioned maple syrups. While most off-flavor buddy (VR5) maple syrup samples tested have both ethanol and DMDS, 1708-06849 has the highest DMDS content of all syrups tested, but no alcohol, while syrup with sap defect (VR1) RUrbain/Bio-C1 does not contain any of these compounds.

Given the very low level of DMDS detected in the samples, an olfactory test was performed in the laboratory to assess whether such concentrations were noticeable. A solution at 0.004 µL/100 g was thus prepared and smelled by five people. In a unanimous opinion, the test participants ruled that the sulfur odor characteristic of this higher concentration compound was not perceptible. Although very subjective, this test tends to validate the fact that the "vegetal" smell of off-flavor buddy (VR5) maple syrups does not come, at least not entirely, from DMDS.

The elemental compositions of the off-flavor maple syrup samples deduced through high-resolution mass spectrometry as detailed above revealed that the molecules likely to be involved in the taste defect often contain nitrogen, which could explain the unpleasant smell and taste of off-flavor industrial grade syrups, since amines often have foul smells.

EXAMPLE 10

Reanalysis of Maple Samples Classified by Centre ACER

Maple syrup samples previously classified by Centre ACER were reanalyzed with the method of the present invention by contacting the maple syrup samples with gold nanoparticles of 15 nm for 600 seconds. Table 27 below shows the comparative results from samples that were classified as VR5 and good tasting by Centre ACER.

TABLE 27

Results obtained from the analysis of VR5 or regular maple syrup samples classified by Centre ACER

| Classification by method of the present invention | Off-Flavor (VR5) samples according to Centre ACER (%) | Good tasting samples according to Centre ACER (%) |
|---|---|---|
| Negative | 2 | 71 |
| Positive | 82 | 15 |
| Uncertain/Transition point | 5 | 8 |
| Sappy taste (green) | 11 | 6 |

The classification by Centre ACER is performed with a subjective taste test, which is prone to error as the person performing the taste may not detect subtle differences in taste from off-flavor samples that are only lightly so. The method of the present invention was able to find that 82% of samples classified as VR5 were indeed appropriately classified, with 5% remaining uncertain as to the nature of their defect, and 11% having a sappy-flavor instead of an off-flavor VR5 taste. Therefore, the method of the present invention represents a net improvement in the classification of samples with taste defects. Importantly, the method of the present invention was able to identify that only 71% of samples that were classified as good flavor by Centre Acer were indeed good flavor. 15% of good flavor samples were in fact VR5 samples, while another 14% were in the transition region of the test (8%) and sappy-flavor (6%) instead of a good flavor sample. To clarify, the transition region is denoted from the spectrophotometric data corresponding to the change in color of the test. These samples were almost equally classified as good-tasting or bad-tasting by Centre Acer, demonstrating the difficulty of making the proper classification with a subjective test. Therefore, the present invention represents a net improvement in the classification of samples with apparent good taste when in fact they do possess a taste defect, particularly the off-flavor VR5 taste defect.

EXAMPLE 11

Screening for Identification of Compounds Reacting with Nanoparticles

To identify the potential compound or compounds which could explain the unpleasant smell and taste of off-flavor industrial grade syrups, diverse amino acids and compounds were diluted in 100 µL of water, 100 µL of a sucrose solution containing 66% of sucrose (an amount of sucrose similar to the amount found in maple syrup at 66° Brix), as well as 100 µL of maple syrup were contacted with 1.900 mL of nanoparticles for 600 seconds, and the colorimetric shift of the solutions was visually assessed. The amino acids tested are shown in Table 27 below, and the compounds tested are shown in Table 28 below.

TABLE 28

Amino acids tested as potential compounds reacting with nanoparticles.

| Amino acids | Detected in maple syrup | Water* | Sucrose* | Syrup* |
|---|---|---|---|---|
| Methionine | Yes (Sap - 10-15° B) 0.01-28 µM | ND | >500 µM | >0.5 µM |
| Glutamine | Yes (Sap - 10-15° B) 0.05-195 µM | ND | ND | ND |
| Histidine | Yes (Sap - 10-15° B) 0.1-91 µM | ND | ND | 5 µM |
| Glycine | Yes (Sap - 10-15° B) 0.05-9 µM | ND | ND | ND |
| Glutamic Acid | Yes (Sap - 10-15° B) 0.5-340 µM | ND | ND | ND |
| Cysteine | Yes (Sap - 10-15° B) 0.01-0.18 µM | >500 µM | 500 µM | 0.5 µM |
| Lysine | Yes (Sap - 10-15° B) 0.03-0.77 µM | ND | ND | 500 µM |
| Serine | Yes (Sap - 10-15° B) 0.01-5.5 µM | ND | ND | ND |

ND: Not detected

TABLE 29

Molecules tested as potential compounds reacting with nanoparticles.;

| Molecules | Detected in maple syrup | Water* | Sucrose* | Syrup* |
|---|---|---|---|---|
| Pyrazine | Yes 49-77 ng/g | ND | ND | ND |
| 4-MercaptoPyrdine | No | 5 μM | 5 μM | 5 μM |
| DMDS | Yes | 50 μM | 50 μM | >50 μM |
| Adenosine | Yes, +derivatives | 50 μM | 50 μM | 5 μM |
| Purine | Derivatives only | ND | ND | 5 μM |
| Imidazole | No | >5 μM | 50 μM | >50 μM |
| Pyridine | No | 5 μM | 50 μM | >50 μM |
| Glucose | Yes, ≈4% of sugars | ND | ND | ND |
| Homovanillic Acid | No, but similar to Vannilin | ND | ND | ND |
| Mandelic Acid | No | ND | ND | ND |
| Benzylmalonic Acid | No | ND | ND | ND |
| 2-Pyrazine Carboxylic Acid | No | ND | ND | >500 μM |
| Phenol | No | ND | ND | ND |
| 3-Methoxy Phenylacetic Acid | No, but similar to Syringic acid (≈1 μg/g) | ND | ND | ND |
| 4-Amino Phenyl Acetic Acid | No | ND | ND | ND |
| Vannilin | Yes 1-3 μg/g [1] | ND | ND | ND |
| Allantonin | Yes [2] | ND | ND | ND |

ND: Not detected

Figure 19:
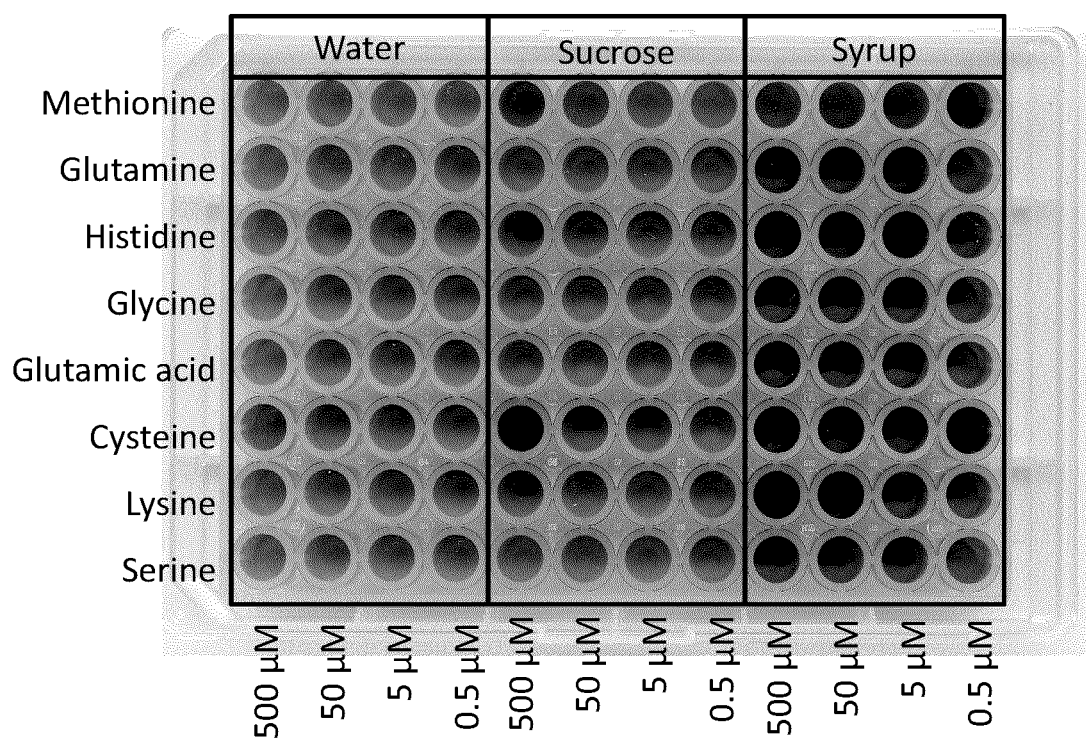
FIG. 19 illustrates the colorimetric assessment of different amino acids found in maple sap, at decreasing concentrations from 500 µM to 0.5 µM, in water, sucrose, or maple syrup contacted with nanoparticles according to an embodiment of the present invention.
Figure 20:
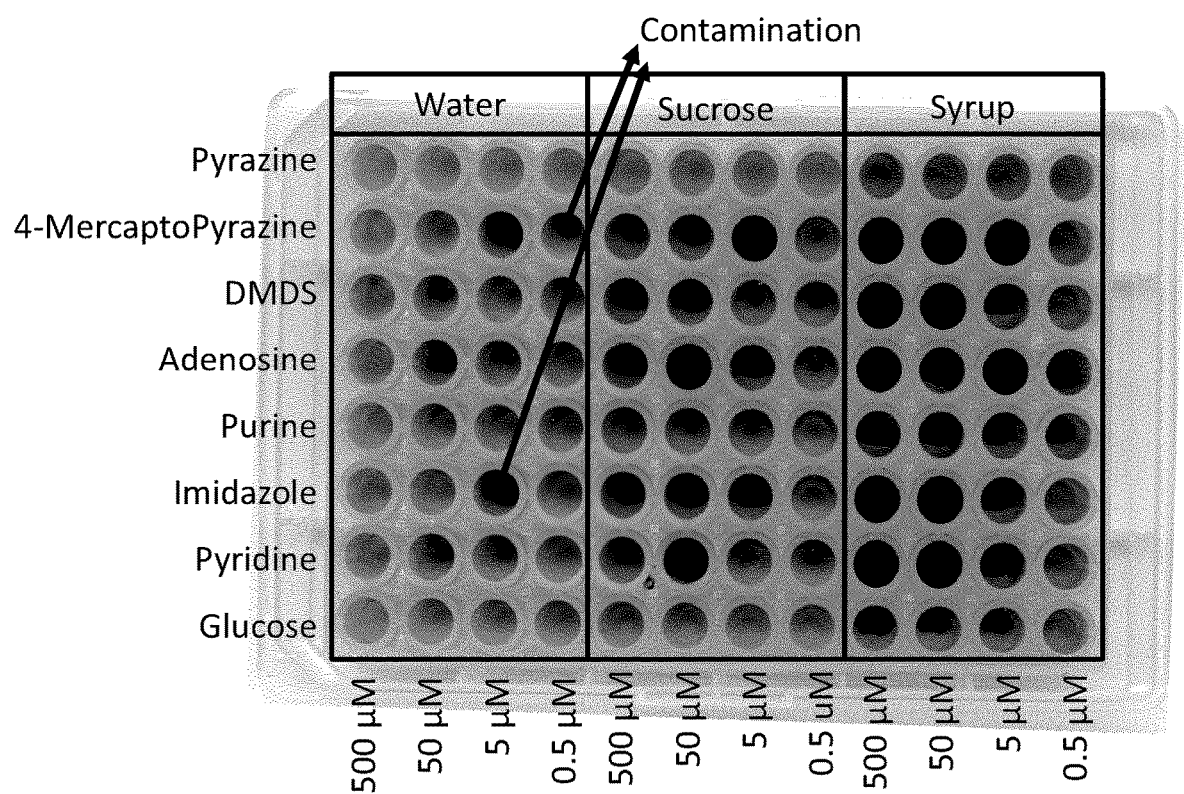
FIG. 20 illustrates the colorimetric assessment of different compounds, at decreasing concentrations from 500 µM to 0.5 µM, in water, sucrose, or maple syrup contacted with nanoparticles according to an embodiment of the present invention
Figure 21:
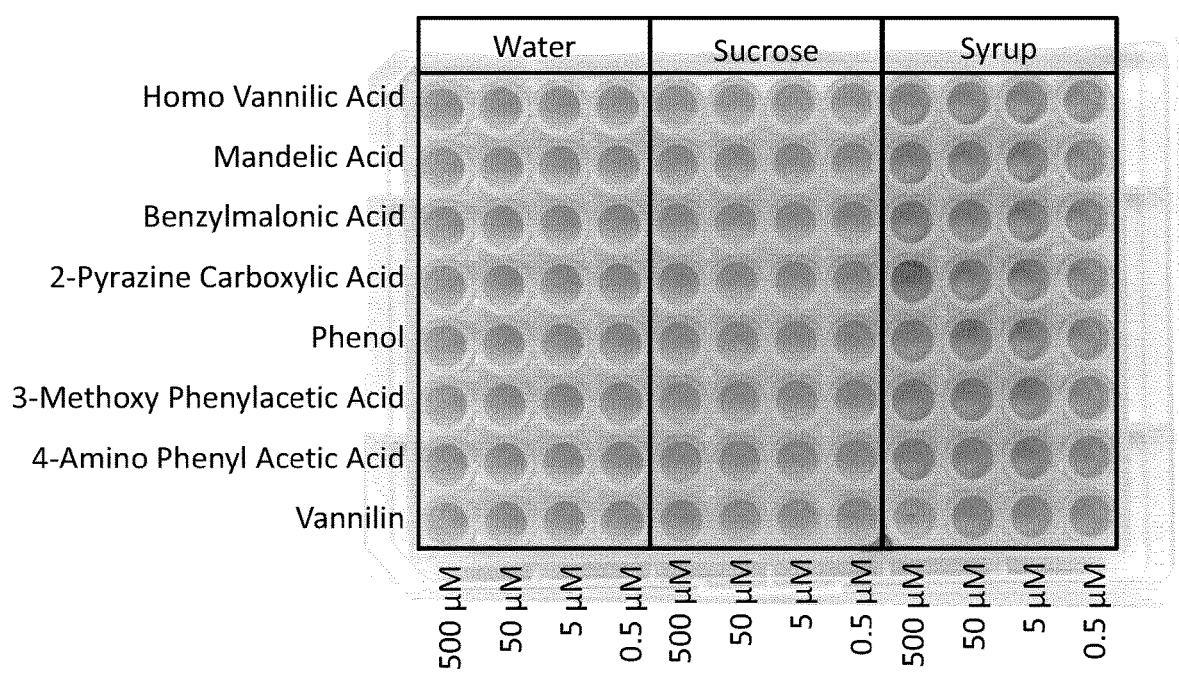
FIG. 21 illustrates the colorimetric assessment of different compounds, at decreasing concentrations from 500 µM to 0.5 µM, at varying concentrations in water, sucrose, or maple syrup contacted with nanoparticles according to an embodiment of the present invention

The results are presented in FIGS. 19 to 21. Now referring to FIG. 19 and Table 27, the amino acid methionine can be detected in sucrose starting at concentrations larger than 500 μM, and in maple syrup at concentrations larger than 0.5 μM. The amino acid cysteine can be detected in water starting at concentrations larger than 500 μM and sucrose starting at concentrations of 500 μM, and in maple syrup at concentrations of 0.5 μM. The amino acid lysine can be detected in water starting at concentrations of 500 μM.

Now referring to FIG. 20 and Table 28, the molecule 4-Mercaptopyrdine can be detected in all medium at concentrations of 5 μM, DMDS can be detected in all medium at concentrations larger than 50 μM. Adenosine can be detected in water and sucrose at concentrations of at least 50 μM, and in maple syrup at concentrations of at least 5 μM. Purine can be detected maple syrup at concentrations of 5 μM. Imidazole can be detected in water at concentrations of at least 5 μM, in sucrose at concentrations of at least 50 μM, and in maple syrup at concentrations larger than 50 μM. Pyridine can be detected in water at concentrations of 5 μM, in sucrose at concentrations of 50 μM, and in maple syrup at concentrations larger than 50 μM. 2-Pyrazine carboxylic acid can be detected maple syrup at concentrations larger than 500 μM.

EXAMPLE 12

Spectrophotometric Analysis of Dilutions of Maple Syrup Sample

Figure 22:
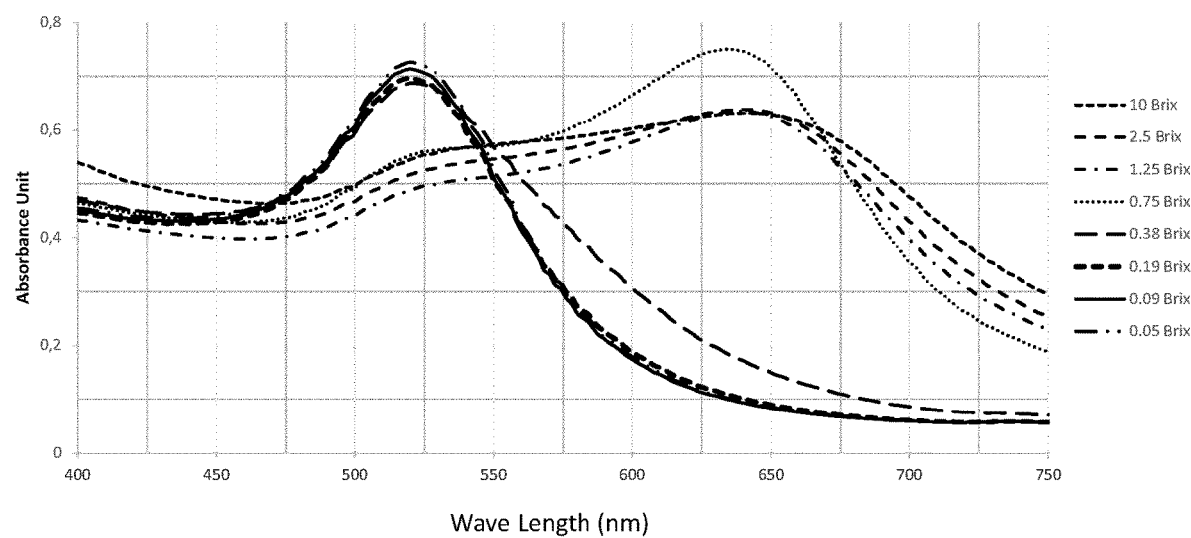
FIG. 22 illustrates the absorbance spectra of colorimetric tests performed with different concentrations of a 2018 end-of-season maple sap concentrate sample.

Now referring to FIG. 22. In order to determine the limit of detection of the colorimetric test in a scenario where a buddy flavoured maple syrup sample was diluted in a good flavoured maple syrup, different mixtures were produced by mixing a buddy flavoured maple syrup sample in a good flavoured maple syrup in different ratios. Gold nanoparticles were added to each sample containing good and off-flavor buddy maple syrup to observe the resulting absorbance spectra. The absorbance value at 625 nm started to be higher than the absorbance value at 625 nm for the sample produced from 75% of a buddy flavoured maple syrup. The limit of detection of the colorimetric test these conditions was around 60% of a buddy flavoured maple syrup.

EXAMPLE 13

Evaluation of Reaction Time

Figure 23:
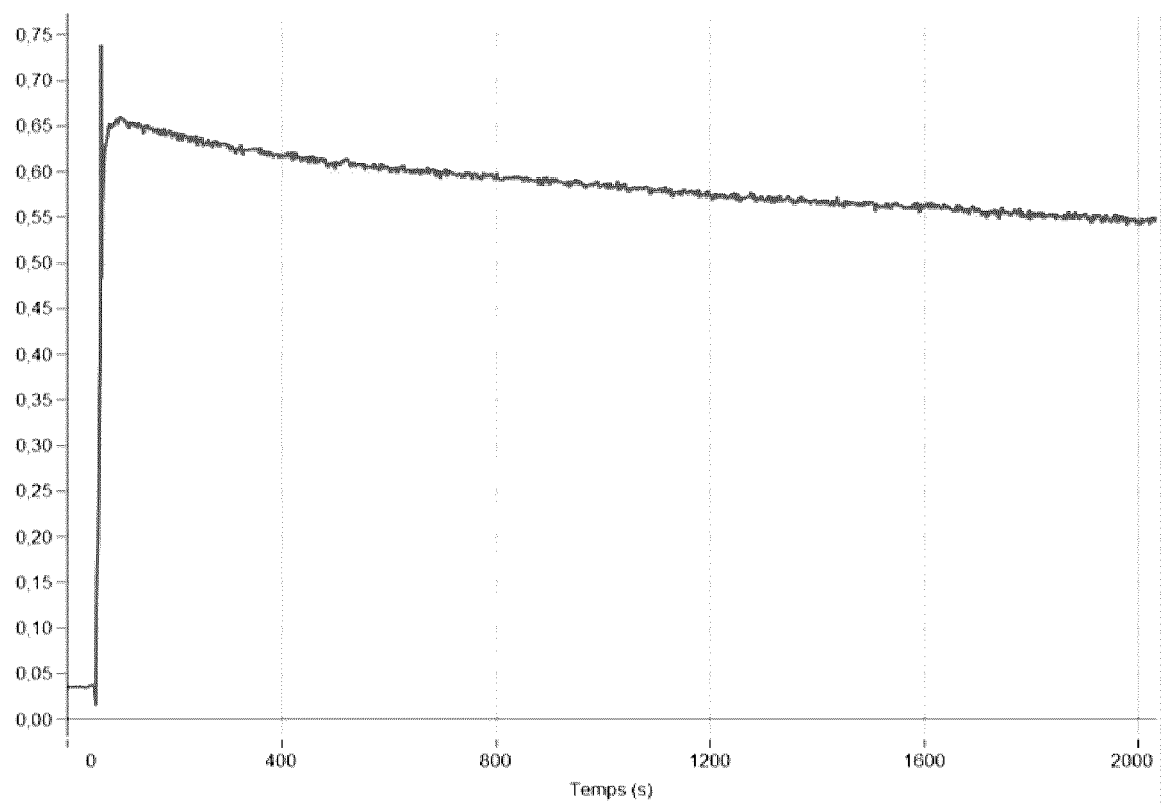
FIG. 23 illustrates the absorbance at 625 nm as a function of time for a colorimetric test carried out on a maple syrup VR5. The addition of maple syrup is at T=100 sec.

Now referring to FIG. 23, in order to identify the optimal reaction time for the colorimetric test, the kinetic of the reaction has been studied. Off-flavor buddy maple syrup was added to the gold nanoparticles solution while a spectrophotometer recorded the absorbance variation over time at 625 nm. A maximum is quickly observed following the addition of the off-flavor buddy maple syrup sample. A slow decrease in absorbance is then observed caused by further aggregation of nanoparticles. The optimal waiting time as been determined as from about 300 to about 600 sec.

EXAMPLE 14

Evaluation of pH Effect on the Absorbance

Figure 24:
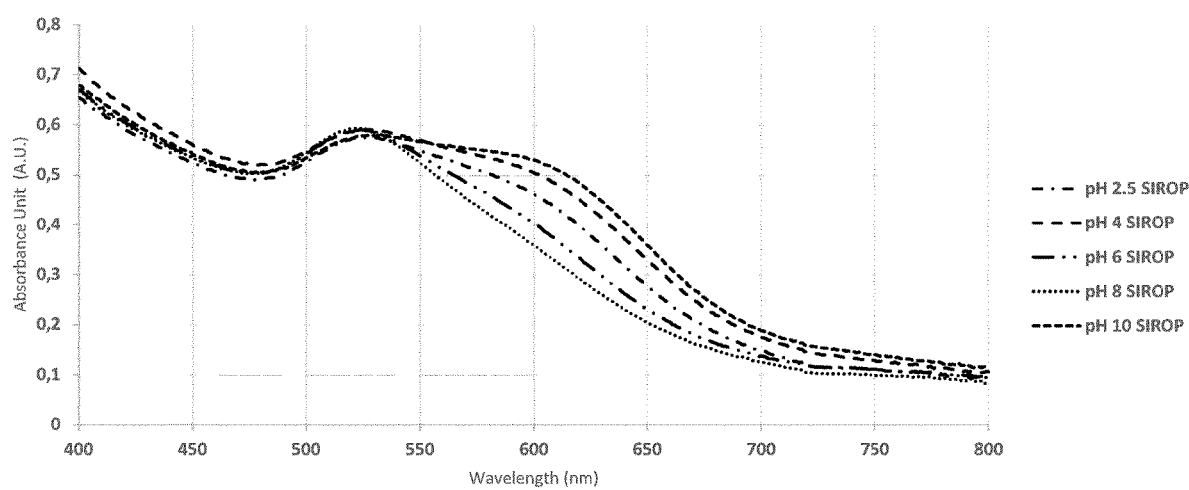
FIG. 24 illustrates the absorbance spectra of a "regular" maple syrup doped with aqueous solutions of different pHs between 2.5 and 10.
Figure 25:
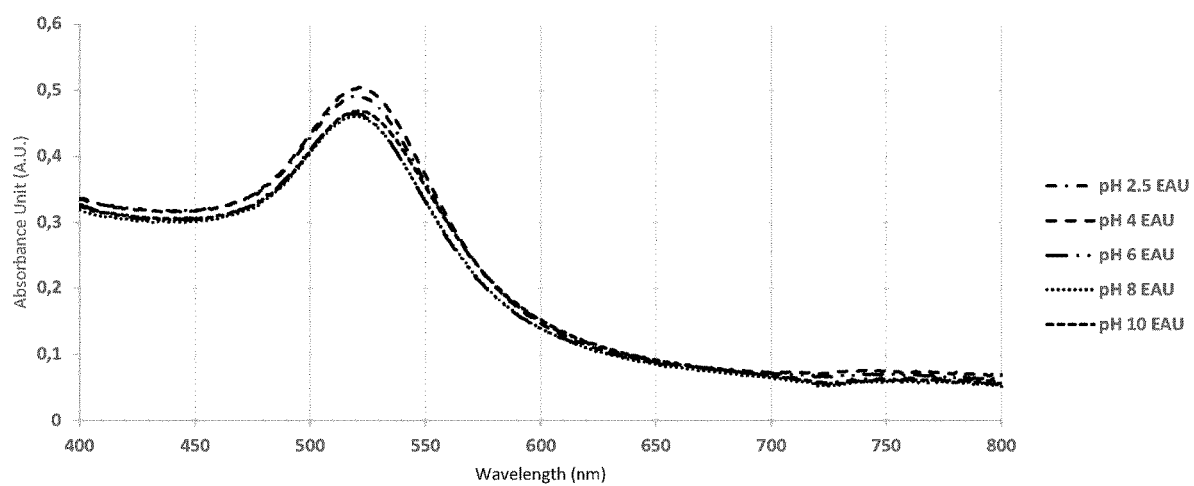
FIG. 25 illustrates the absorbance spectra of colorimetric tests in water doped with aqueous solutions of different pHs between 2.5 and 10.
Figure 26:
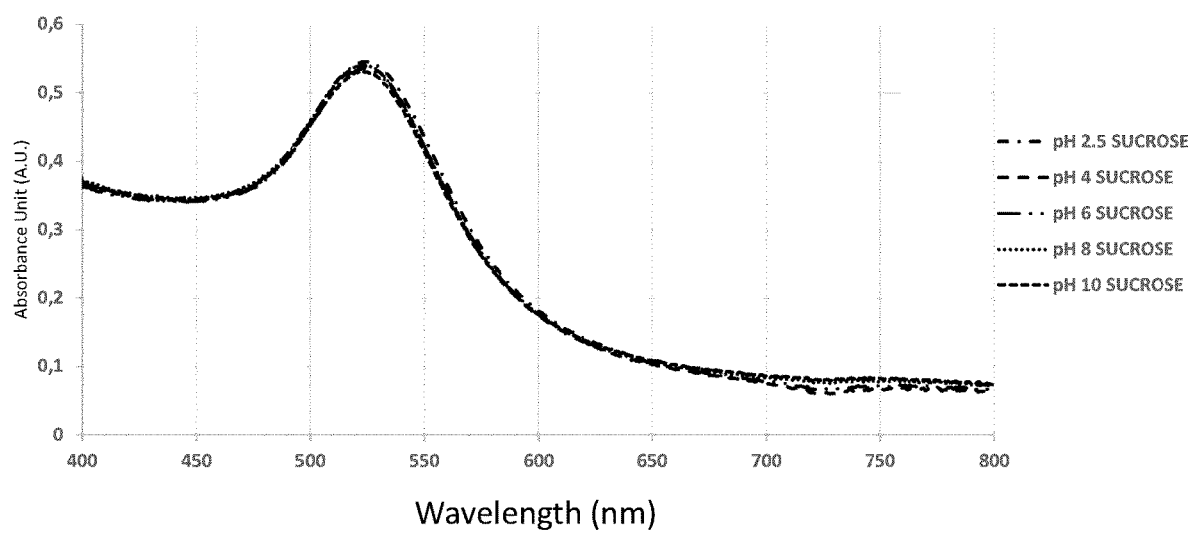
FIG. 26 illustrates the absorbance spectra of colorimetric tests with sucrose solutions at 66° Brix doped with aqueous solutions of different pHs between 2.5 and 10.

Now referring to FIGS. 24-26, in order to determine the effect of maple syrup's pH on the result of the colorimetric test, a good flavour maple syrup sample as been spiked with aqueous acid and basic solutions between pH of 2.5 and 10. A significant absorbance increase is observed at pH values above 8 and below 4. Since maple syrup typically has pH values around 6.5 to 7.5, pH of the maple syrup samples has a low impact on the final result of the colorimetric test. No absorbance variation as been observed in similar experiments in water and sucrose solution spiked with the same acidic and basic solutions.

EXAMPLE 15

Evaluation of ° Brix Effect on Absorbance

Figure 27:
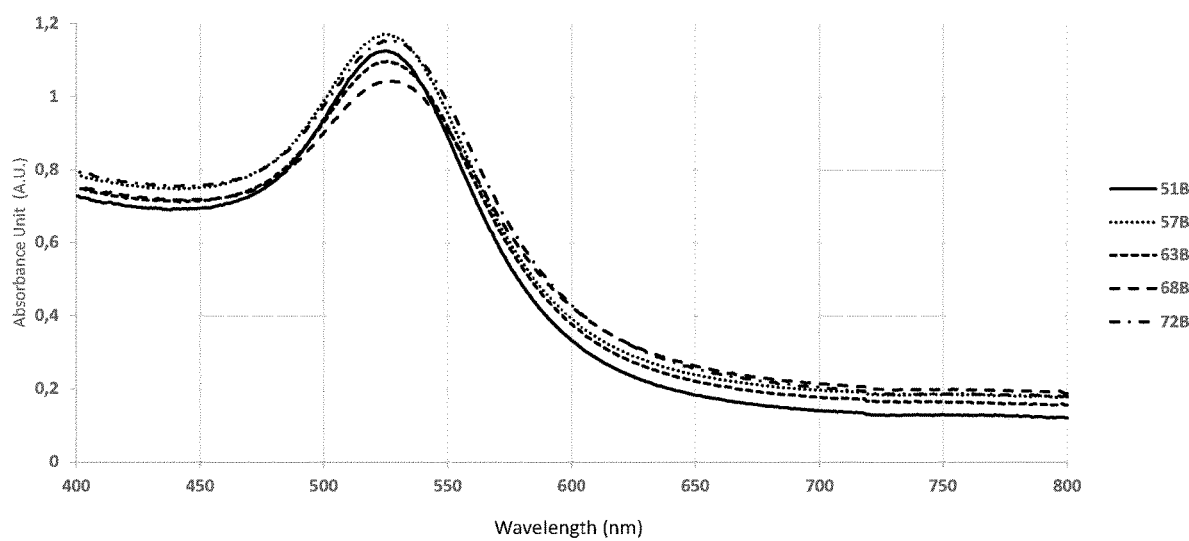
FIG. 27 illustrates the absorbance spectra of colorimetric tests with sucrose solutions at different ° Brix. B=° Brix.

Now referring to FIG. 27, in order to determine the effect of ° Brix variation in maple syrup sample on the final result of the colorimetric test, a gold nanoparticles solution was added to different of sucrose and water solutions with ° Brix between 51 and 72. No significant absorbance variation has been observed.

While preferred embodiments have been described above and illustrated in the accompanying drawings, it will be evident to those skilled in the art that modifications may be made without departing from this disclosure. Such modifications are considered as possible variants comprised in the scope of the disclosure.

The invention claimed is:

1. A method for the detection of an off-flavor buddy maple sap or an off-flavor maple syrup made from buddy maple sap comprising contacting a sample of maple syrup or maple sap with a nanoparticle reactive with a buddy sample of maple syrup or maple sap having a size of from about 1 nm to about 250 nm, and measuring a spectrophotometric property of the nanoparticle in contact with the sample of maple syrup or maple sap,
   wherein
      a change in said spectrophotometric property relative to a same type of spectrophotometric property measurement made on a good flavor maple syrup or maple sap sample, is associated with an off-flavor maple syrup or sap sample, and no change in said spectrophotometric property relative to a same type of spectrophotometric property measurement made on a good flavor maple syrup or maple sap sample, is associated with a good flavor maple syrup or maple sap sample.

2. The method of claim 1, wherein said nanoparticle reactive with a buddy sample of maple syrup or maple sap is selected from the group consisting of a metallic nanoparticle, a metallic coated nanoparticle, a semi-conducting nanoparticle, or combinations thereof.

3. The method of claim 2, wherein a metal of said metallic nanoparticle or said metallic coated nanoparticle is selected from the group consisting of gold, copper, iridium, platinum, rhodium, or an alloy thereof, and combinations thereof, or wherein said semi-conducting nanoparticle is selected from the group consisting of a quantum dot, a carbon dot, and combinations thereof.

4. The method of claim 2, wherein said metallic nanoparticle is in the shape of a sphere, a rod, a rice-grain, a cube, a pyramid, a cage, a disk, or combinations thereof.

5. The method of claim 1, wherein said nanoparticle reactive with a buddy sample of maple syrup or maple sap has a size of about 15 nm.

6. The method of claim 1, wherein said nanoparticle reactive with a buddy sample of maple syrup or maple sap further comprises a coating.

7. The method of claim 6, wherein said coating is an acidic compound.

8. The method of claim 7, wherein said acidic compound is a citrate.

9. The method of claim 1, wherein said sample of maple syrup or maple sap is contacted with a reducing agent prior to or during contact with said nanoparticle.

10. The method of claim 9, wherein said reducing agent is selected from the group consisting of dithiobutylamine, 2-mercaptoetahnol, 2-mercaptoethylamine, cysteine, dithiothreitol (DTT), tris (2-carboxyethyl) phosphine (TCEP), or combinations thereof.

11. The method of claim 1, wherein said change in said spectrophotometric property is a change of color, a change in absorbance, transmittance, diffusion, refractive index or a combination of these measurements.

12. The method of claim 11, wherein said change of color is a change from red to blue.

13. The method of claim 11, wherein said change in absorbance is any one of:
 1. an increase in absorbance at a wavelength of about 400 nm to about 1000 nm, relative to an absorbance measurement made on a good flavor maple syrup or maple sap sample;
 2. a differential absorbance from the absorbance at any wavelength superior to a maximum wavelength of absorption of said nanoparticle in a good flavor maple syrup or maple sap sample and the absorbance at said maximum wavelength of absorption of said nanoparticle in said maple syrup or maple sap sample;
 3. a differential absorbance from a wavelength where absorbance remains stable in any said off-flavor or said good flavor maple syrup or maple sap sample and a wavelength where absorbance changes in said off-flavor maple syrup or maple sap sample;
 4. a differential absorbance between any one wavelength ≥561 nm to 1000 nm and any one wavelength between about 5560 nm wavelength and below;
 5. a differential absorbance between any one wavelength between ≥560 nm to about 1000 nm and absorbance at any one wavelength between about 490 nm to about 560 nm;
 6. a differential absorbance between absorbance at 610 nm and absorbance at any one wavelength between about 490 nm to about 560 nm, and/or between absorbance at 630 nm and absorbance at any one wavelength between about 490 nm to about 560 nm, and/or between absorbance at 640 nm and absorbance at any one wavelength between about 490 nm to about 560 nm; and
 7. a change of a wavelength of maximum absorption to a higher wavelength in the off-flavor maple syrup or maple sap sample, compared to a good tasting maple syrup or maple sap sample.

14. The method of claim 13, wherein a positive differential absorbance is associated to an off-flavor maple syrup or maple sap sample.

15. The method of claim 13, wherein a negative differential absorbance is associated to a good flavor maple syrup or maple sap sample.

16. The method of claim 1, wherein said off-flavor buddy maple sap is a maple sap contaminated with buddy maple sap, buddy maple syrup or combinations thereof.

17. The method of claim 1, wherein said sample of maple syrup or maple sap is a diluted maple syrup sample, a pure maple syrup sample, a diluted maple sap sample, a pure maple sap sample, a diluted maple sap concentrate sample, or a pure maple sap concentrate sample.

18. The method of claim 17, wherein said diluted maple syrup sample, said diluted maple sap sample or said diluted maple sap concentrate sample is diluted from about 1:1 to 1:1000 in a solvent.

19. The method of claim 18, wherein said solvent is water or an organic solvent, or combinations thereof.

20. The method of claim 1, wherein concentration of said nanoparticle is from about 0.1 nM to about 100 nM.

21. The method of claim 1, wherein contacting said sample of maple syrup or maple sap from about 1 second to about 30 minutes.

* * * * *